(12) United States Patent
Brard et al.

(10) Patent No.: US 9,024,039 B2
(45) Date of Patent: May 5, 2015

(54) HETEROCYCLES AND DERIVATIVES THEREOF AND METHODS OF MANUFACTURE AND THERAPEUTIC USE

(75) Inventors: Laurent Brard, Warwick, RI (US);
Satyan Kalkunte, Barrington, RI (US);
Rakesh Kumar Singh, Barrington, RI (US)

(73) Assignee: Women & Infants' Hospital of Rhode Island, Providence, RI (US)

( * ) Notice: Subject to any disclaimer, the term of this patent is extended or adjusted under 35 U.S.C. 154(b) by 833 days.

(21) Appl. No.: 12/096,857

(22) PCT Filed: Dec. 12, 2006

(86) PCT No.: PCT/US2006/047320
§ 371 (c)(1),
(2), (4) Date: Dec. 4, 2008

(87) PCT Pub. No.: WO2007/070494
PCT Pub. Date: Jun. 21, 2007

(65) Prior Publication Data
US 2009/0221529 A1 Sep. 3, 2009

Related U.S. Application Data

(60) Provisional application No. 60/749,405, filed on Dec. 12, 2005.

(51) Int. Cl.
*C07D 249/08* (2006.01)
*C07D 249/12* (2006.01)
*C07D 487/04* (2006.01)

(52) U.S. Cl.
CPC .................................. *C07D 487/04* (2013.01)

(58) Field of Classification Search
USPC ............. 514/80, 248; 544/234, 237; 549/229; 548/263.4, 263.6
See application file for complete search history.

(56) References Cited

U.S. PATENT DOCUMENTS

| 3,710,795 A | 1/1973 | Higuchi et al. | |
| 4,366,320 A * | 12/1982 | Gilbertson | 548/263.6 |
| 4,554,105 A * | 11/1985 | Hesse | 552/653 |
| 4,772,433 A * | 9/1988 | Hesse | 544/233 |
| 5,629,008 A | 5/1997 | Lee | |
| 5,795,882 A | 8/1998 | Bishop et al. | |
| 5,851,547 A | 12/1998 | Fujioka et al. | |
| 6,183,461 B1 | 2/2001 | Matsuura et al. | |
| 7,019,146 B1 * | 3/2006 | Ishigai et al. | 548/103 |
| 8,617,898 B2 * | 12/2013 | Dey et al. | 436/131 |
| 2003/0171605 A1 | 9/2003 | Reddy et al. | 552/653 |
| 2005/0059641 A1 | 3/2005 | Ray et al. | |
| 2013/0137185 A1 * | 5/2013 | Holmquist et al. | 436/140 |

FOREIGN PATENT DOCUMENTS

| JP | 59163364 | 9/1984 | |
| WO | 2005/030222 | 4/2005 | ............ A61K 31/59 |
| WO | WO2005030222 A1 | 4/2005 | |

OTHER PUBLICATIONS

European Search Report of corresponding European Patent Application No. 06845248.1 dated Dec. 17, 2009.
Andrews, David R., et al., "Synthesis of 25-Hydroxy- and 1alpha, 25-Dihydroxyvitamin D3 From Vitamin D2 (Calciferol)", Journal of Organic Chemistry 1986, vol. 51, pp. 4819-4828.
Higashi, T., et al., "Simultaneous Determination of 25-Hydroxyvitamin D2 and 25-Hydroxyvitamin D3 in Human Plasma by Liquid Chromatography-tandem Mass Spectrometry Employing Derivatization with a Cookson-type Reagent", Biol. Pharm. Bull. 2001, 24(7), pp. 738-743.
Shimada, K., et al., "Retention Behavior of Conjugated Metabolites of Vitamin D and Related Compounds in High-Performance Liquid Chromatography", Journal of Chromatographic Science, vol. 32, Mar. 1994.
Feldman, Editorial/Mini-Review: Vitamin D and Prostate Cancer, Endocrinology 141: 5-9 (2000).
Barreto et al., 25-Hydroxyvitamin D3, the Prohormone of 1,25-Dihydroxyvitamin D3, Inhibits the proliferation of Primary Prostatic Epithelial Cells, Cancer Epidemiology, Biomarkers & Prevention 9:265-70 (2000).
Beer et al., Calcitriol in cancer treatment: From the lab to the clinic, Molecular Cancer Therapeutics: 373-81 (2004).
Vijayakumar et al., Clinical Trials involving vitamin D analogs in prostate cancer, Cancer J 11: 362-73 (2005).

* cited by examiner

*Primary Examiner* — Sabiha N Qazi
(74) *Attorney, Agent, or Firm* — Novak Druce Connolly Bove + Quigg LLP; Thomas M. Saunders

(57) ABSTRACT

This invention relates to the design, synthesis and use of synthetic vitamin D and other steroidal analogs. It further relates to the therapeutic use of such analogs and their manufacture.

3 Claims, 18 Drawing Sheets

HETEROCYCLES AND DERIVATIVES THEREOF AND METHODS OF MANUFACTURE AND THERAPEUTIC USE

RELATED CASE INFORMATION

This application is a 371 application based on PCT Application No. PCT/US06/47320, filed Dec. 12, 2006 which claims benefit of Provisional Application No. 60/749,405, filed Dec. 12, 2005.

FIELD OF THE INVENTION

This invention relates to the use of vitamin D analogs. It further relates to the therapeutic use of such analogs and their manufacture.

BACKGROUND

Vitamin D and various vitamin D analogs have been investigated in the past for their therapeutic effects. The following references are representative.

U.S. Patent Publication No. 2005/0059641 published Mar. 17, 2005.

U.S. Pat. No. 5,795,882 issued Aug. 18, 1988.

Feldman, Editorial/Mini-Review: Vitamin D and Prostate Cancer, *Endocrinology* 141: 5-9 (2005).

Barreto et al., 25-Hydroxyvitamin $D_3$, the Prohormone of 1,25-Dihydroxyvitamin $D_3$, Inhibits the proliferation of Primary Prostatic Epithelial Cells, *Cancer Epidemiology, Biomarkers & Prevention* 9: 265-70 (2000).

Beer and Myrthue, Calcitriol in cancer treatment: From the lab to the clinic, *Molecular Cancer Therapeutics*: 373-81 (2004).

Vijayakumar et al., Clinical trials involving vitamin D analogs in prostate cancer, Cancer J 11: 362-73 (2005).

SUMMARY OF THE INVENTION

Vitamin D and various analogs have demonstrated mechanism-based anti-cancer activity and other therapeutic applications for diseases such as psoriasis and anti-inflammatory conditions in animal models and humans. However, pharmacologic doses of vitamin D lead to lethal hypercalcemia. To avoid these unwanted side effects, a large number of synthetic analogs of vitamin D have been developed and used to inhibit tumor progression and metastatic spread in animal models of various cancer types. However, the therapeutic efficacy of systemically applied vitamin D analogs in treating cancer has not yet fulfilled its promise because of hypercalcemia, at the supraphysiological doses needed to reach clinical improvement. Moreover, the analogs described to date are difficult to synthesize and routes of synthesis are unlikely to be commercialized given their complexity. Therefore, the discovery of a non-calcemic, easily synthesized, and potent analog is the ultimate goal of vitamin D research for the treatment of human diseases.

The invention described herein meets this goal. We have achieved the design, synthesis and identification of a potent class of novel antiproliferative molecules. Potent biological activity, short-path high yield syntheses, and significantly improved stability (and therefore drugability) are contemplated within the scope of this invention.

According to the invention, calciferol underwent an efficient Diels-Alder (DA) reaction with 4-methyl-1,2,4-triazoline-3,5-dione to afford the N-methyl (DA) adduct of calciferol, which subsequently was esterified by bromoacetic acid in the presence of dicyclohexyl dicarbodiimide (DCC), pyridine, and dimethylamino pyridine (DMAP) to afford our representative vitamin D analog (HEVD).

This invention includes a compound of the formula selected from the group consisting of:

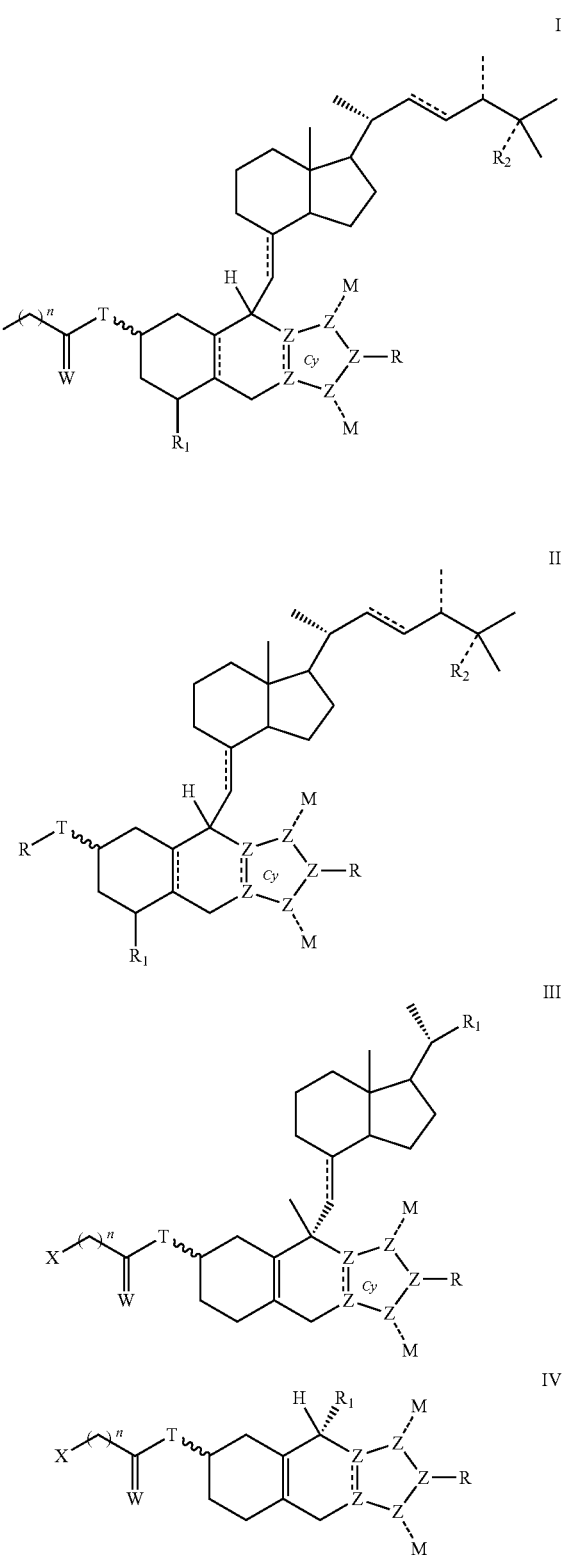

-continued

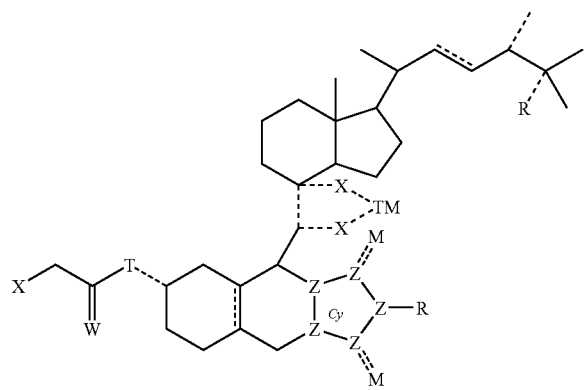

V

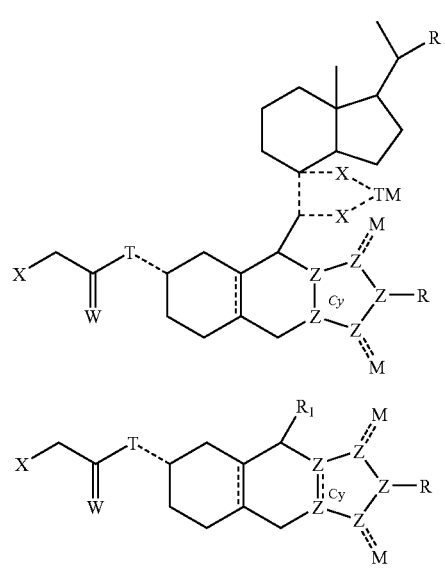

VI

VII wherein Z is C or N
- R is H, amino, hydroxyl, halogen, alkyl, aryl, heteroaryl, arylalkyl
- $R_1$ represents H, OH, OR, NH2, NR2, SH, SR and alkyl.
- $R_2$ represents H, alkyl, alkenyl, alkynyl, aryl, heteroaryl, arylalkyl, heteroarylakyl, OH, COOH, COOR, COR, OR, SH, SR, SOR, $SO_2R$, CHO, halides, $NO_2$, $NH_2$, $NR_1R_2$, peptides, carbamoyl, thiocarbamoyl amides, ureas, thioureas, SO3H, SO3R, CN and derivatives as follows: tetrazoles and oxadiazoles.
- (----) represents a single, double and optical/stereo/geometrical bond isomers,
- M is C, S and N atoms in open and combined forms such as cyclic structures,
- T is O, C, N and S in single, double and suitable higher bonded states such as NH, $NR_2$, and as in $CH_2$,
- TM is a transition metal.
- W is O, C, N S and =CN, =CH—$NO_2$, =N—CN, =N—$NO_2$,
- n is the number of carbon atoms or bio-isosteric replacements thereof,
- and
- Cy is a ring size of from 4 to 10 atoms, and further increasing to any size structurally allowable with the definition of Z as above.

Particular note is made of this compound wherein W is =CN, =CH—$NO_2$, =N—CN, or =N—$NO_2$.

In a specific embodiment this invention comprises a compound comprising Structure IX.

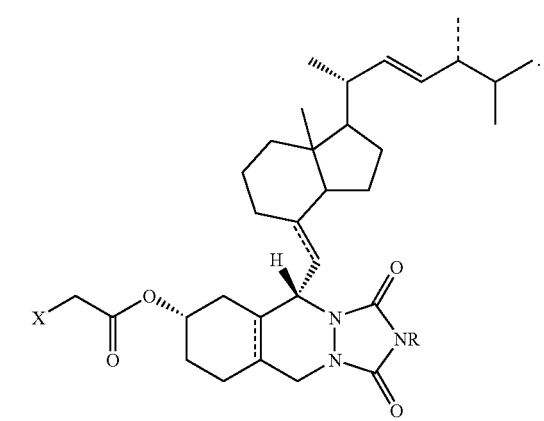

It further comprises a compound comprising Structure X.

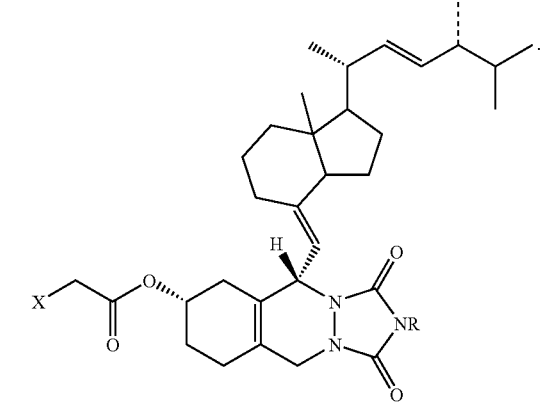

Additionally, a compound comprising Structure XI.

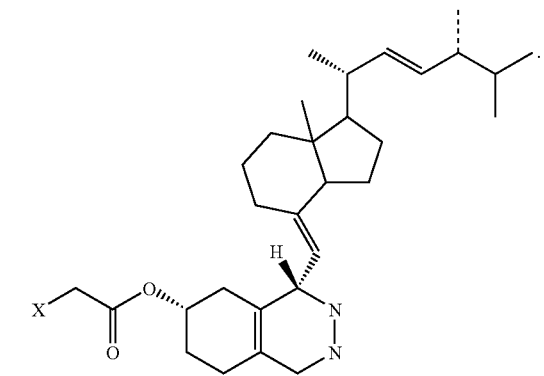

And still further a compound comprising Structure XII.

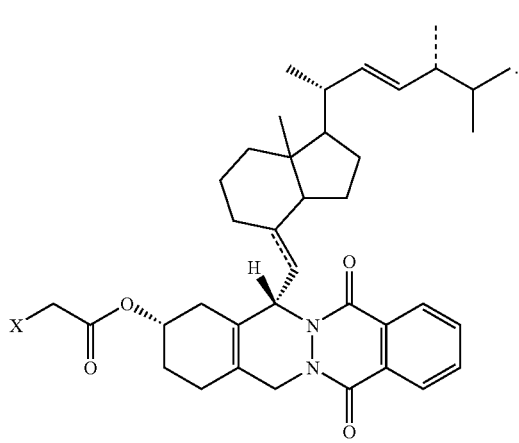

This invention comprises a compound comprising Structure XIII

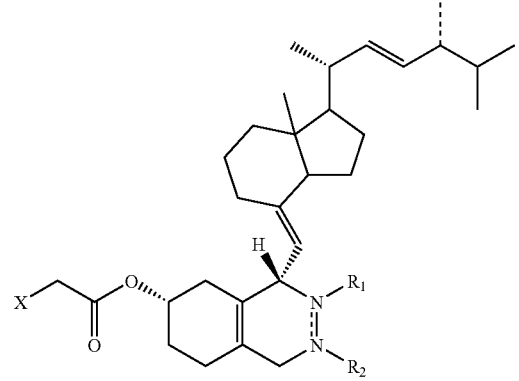

as well as a compound comprising Structure XIV,

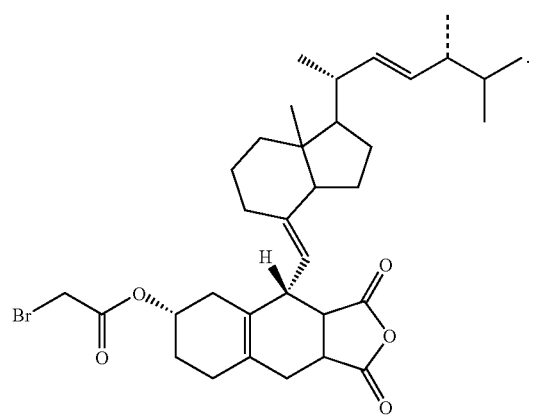

This invention contemplates a compound comprising Structure XV

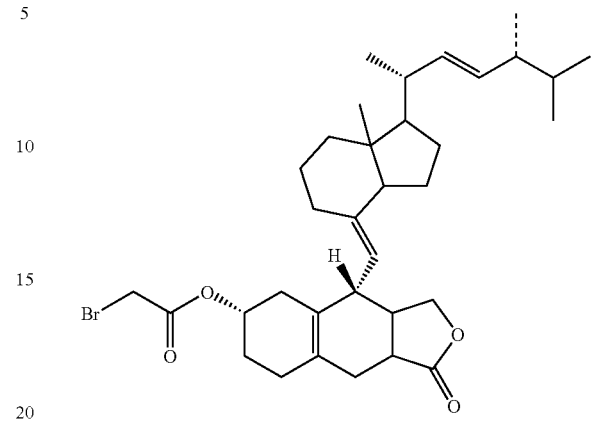

and a compound comprising Structure XVI

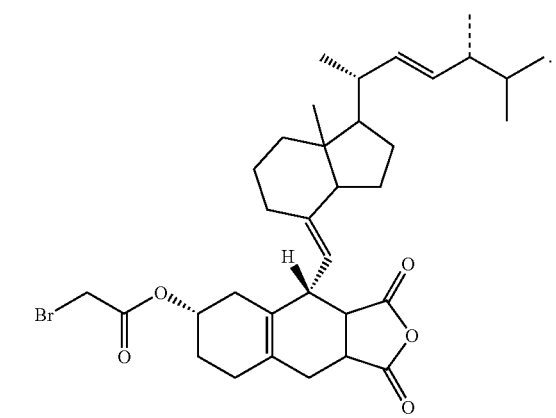 [SMILES: CC(C)[C@@H](C)/C=C/[C@@H](C)C1CCC2/C(=C/[C@H]3C4=C(CC[C@H](OC(=O)CBr)C4)CC4C(=O)OC(=O)C43)CCCC21C]

Note is also made of a compound comprising Structure XVII

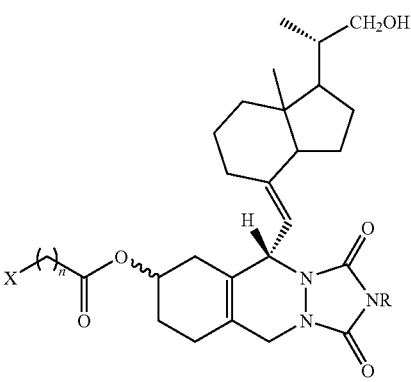

and a compound comprising Structure XVIII

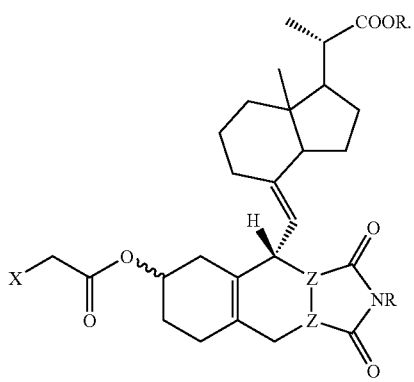

Yet further included is a compound comprising Structure XIX

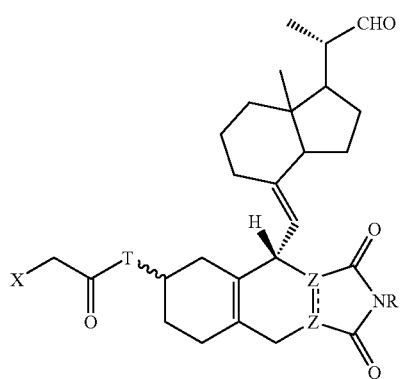

and a compound comprising Structure XX

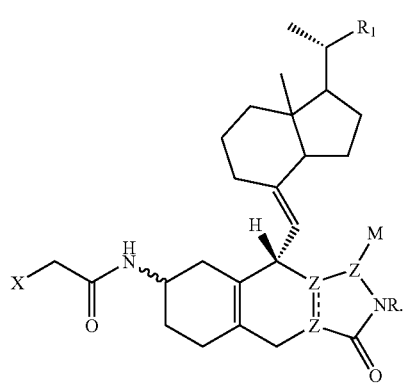

In one embodiment this invention includes a compound of the formula

Structure VIII

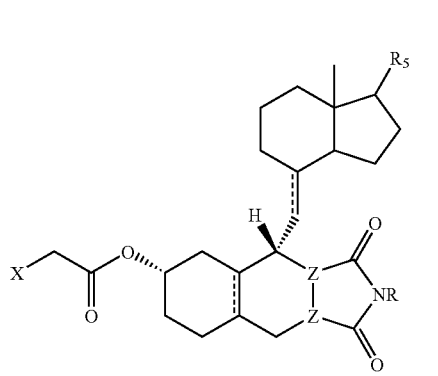

wherein

R is atoms and groups such as H, amino, hydroxyl, halogens and groups of atoms such as alkyl, aryl, heteroaryl, arylalkyl groups and R5 represents the side-chain in structure VIII as exemplified by but not limited to the drawings below.

and $R_5$ is a moiety selected from the group consisting of

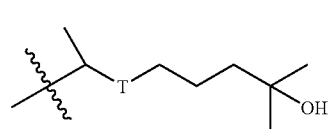
1

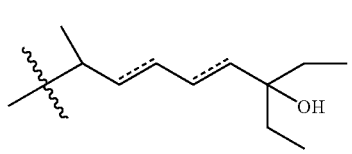
2

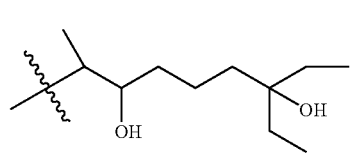
3

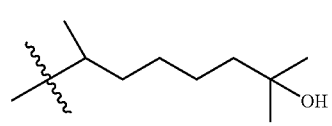
4

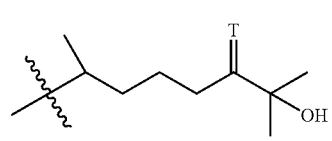
5

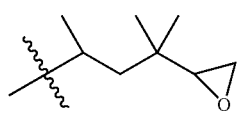
6

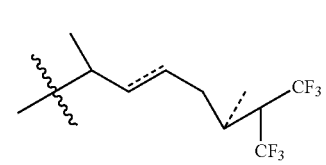
7

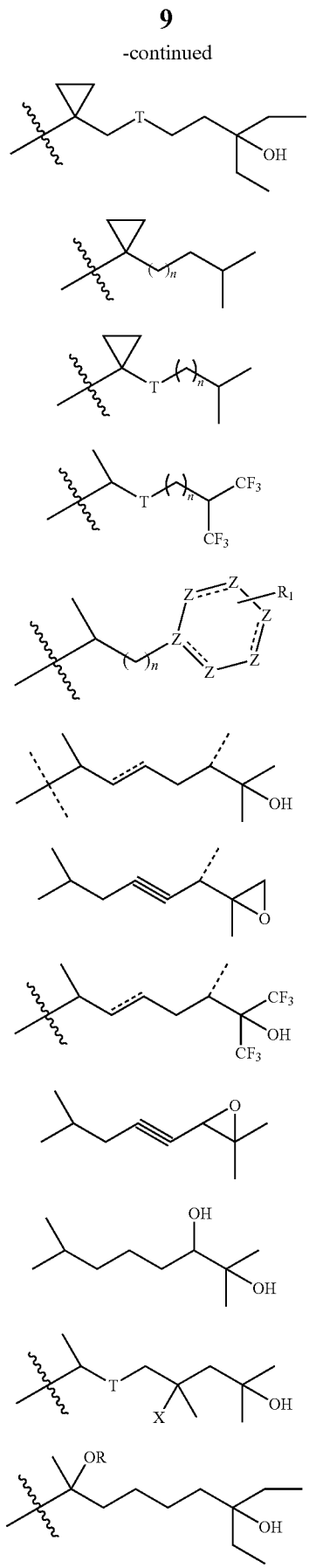
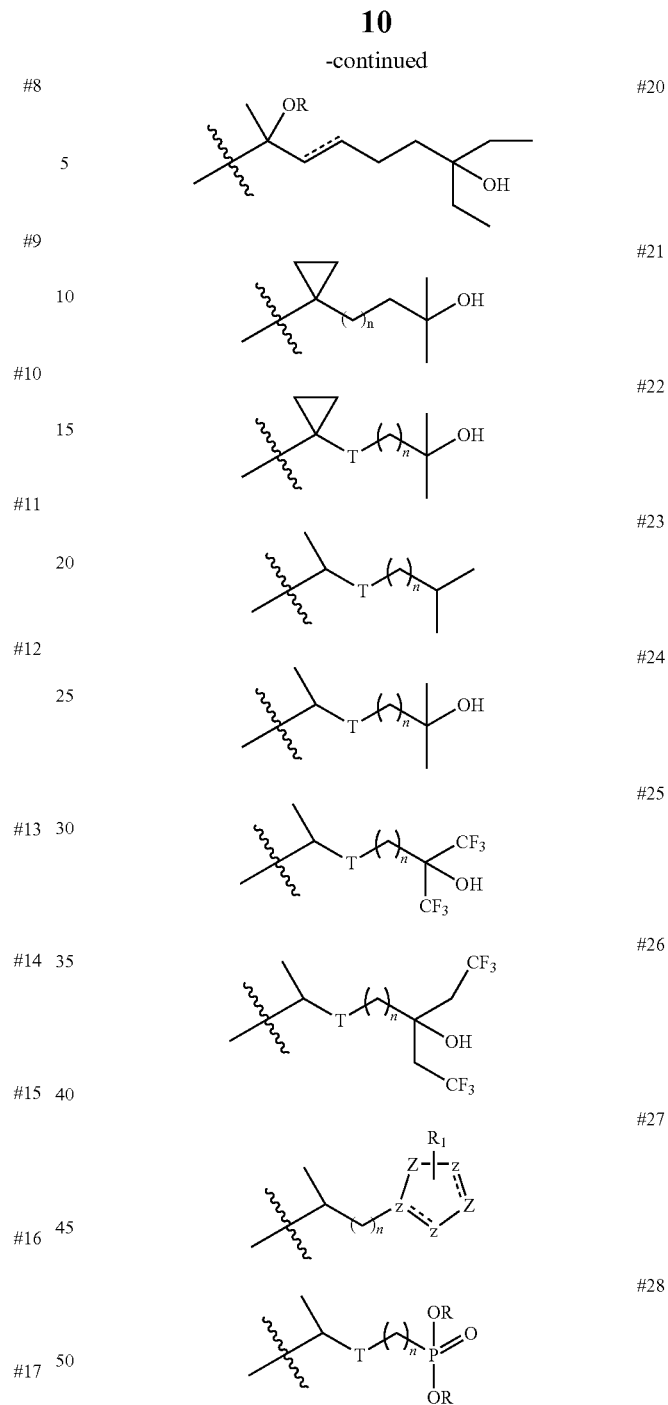

Methods of treatment are further contemplated within this invention with particular reference to a method of treating disease comprising the following step administering a therapeutically effective amount of any of the above noted compounds. Such administration is part of treating disease selected from the group consisting of human solid tumors, psoriasis, rheumatoid arthritis, inflammatory bowel disease, scleroderma, Guillain-Barre syndrome, epilepsy, multiple sclerosis, polyarteritis nodosa and esophagitis.

Within the context of this invention, treatment may be accomplished by administering a therapeutically effective amount of an above noted compound, optionally in combination with at least one additional pharmaceutical compound.

DETAILED DESCRIPTION OF THE INVENTION

Figure 1A:
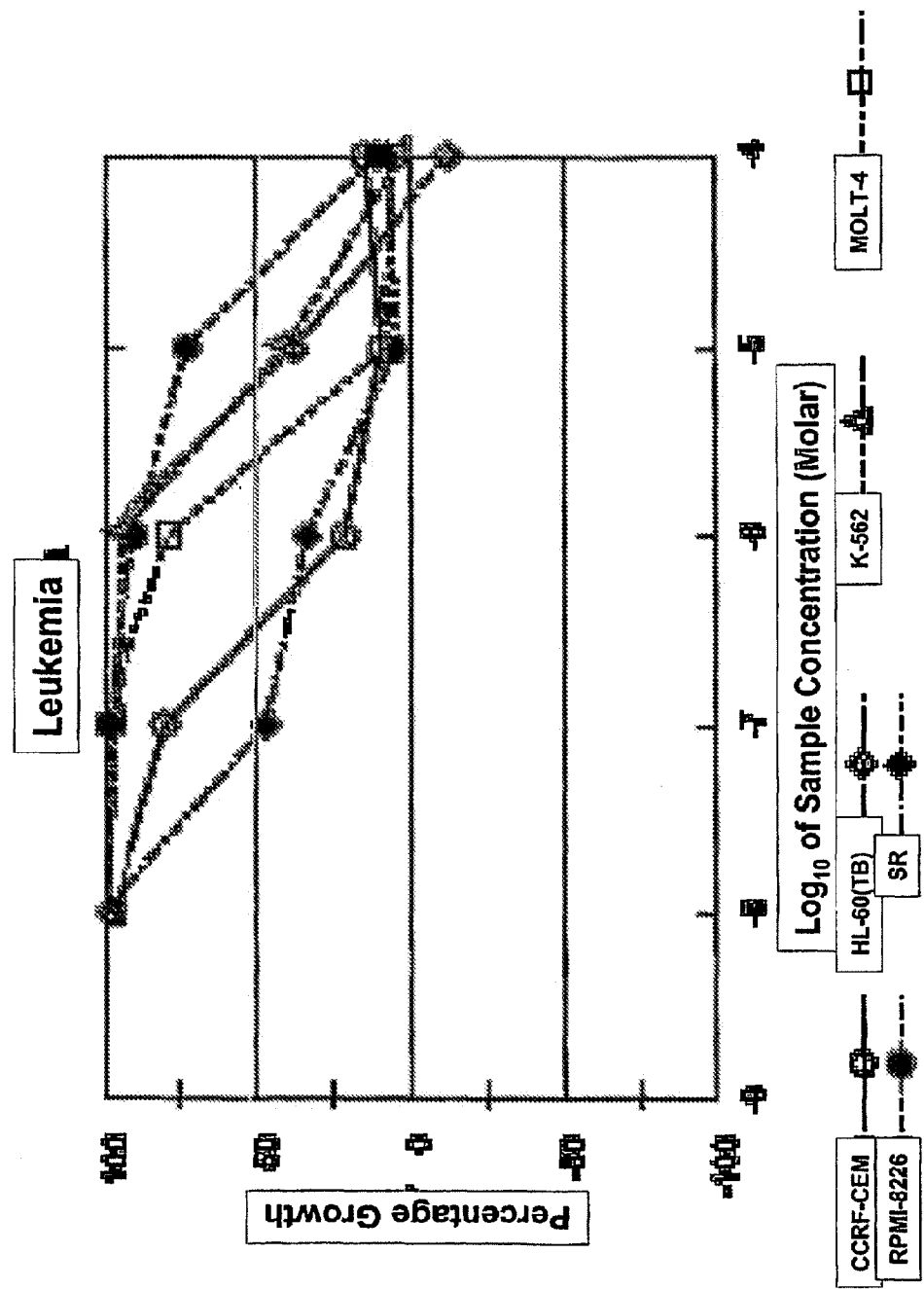
FIG. 1 (a) through (i). Represents graphs of the effect of HEVD analogs (Compound IX where R=methyl and X=Br) on 60 cancer cell lines.
Figure 1B:
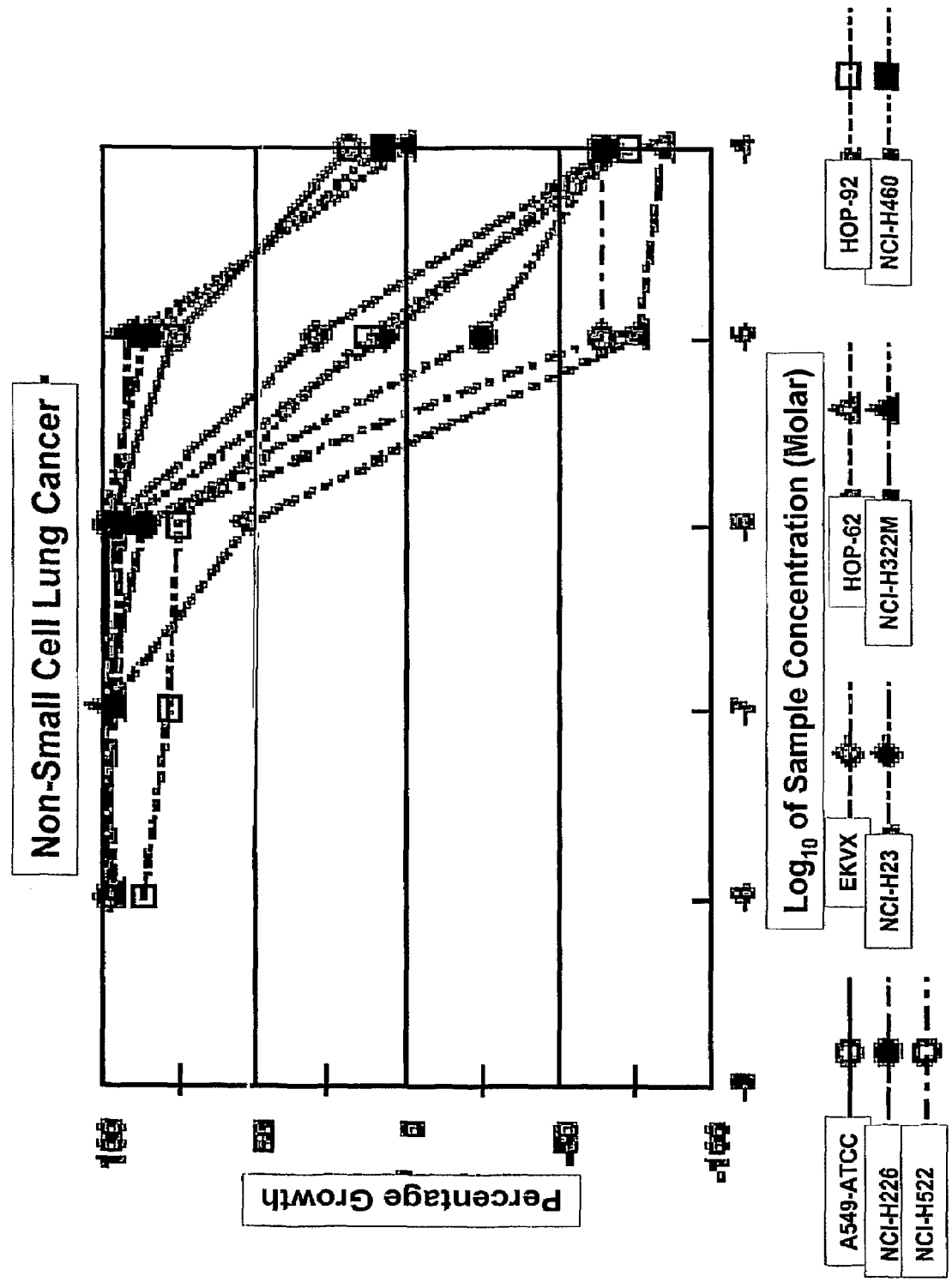
Figure 1C:
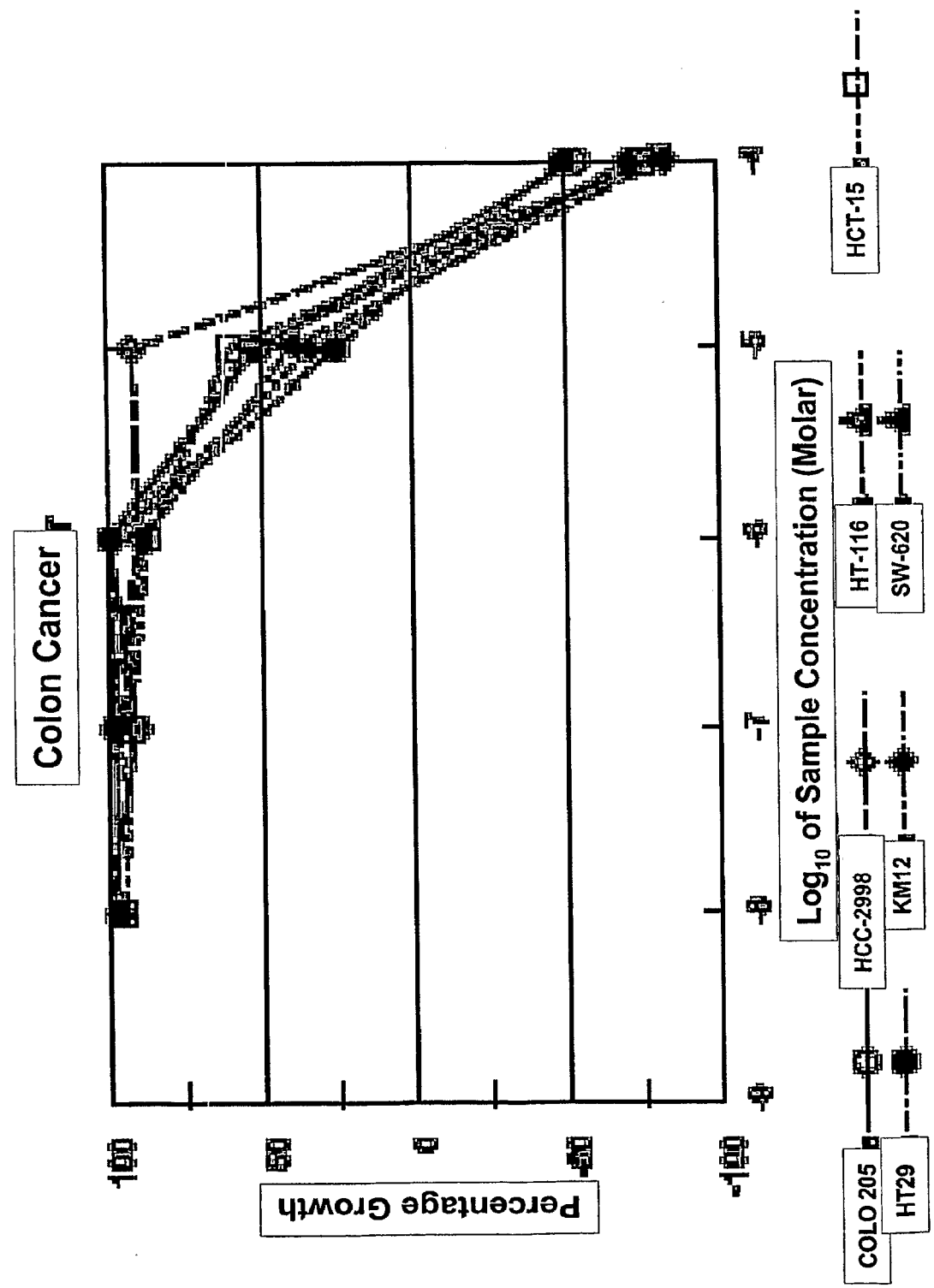
Figure 1D:
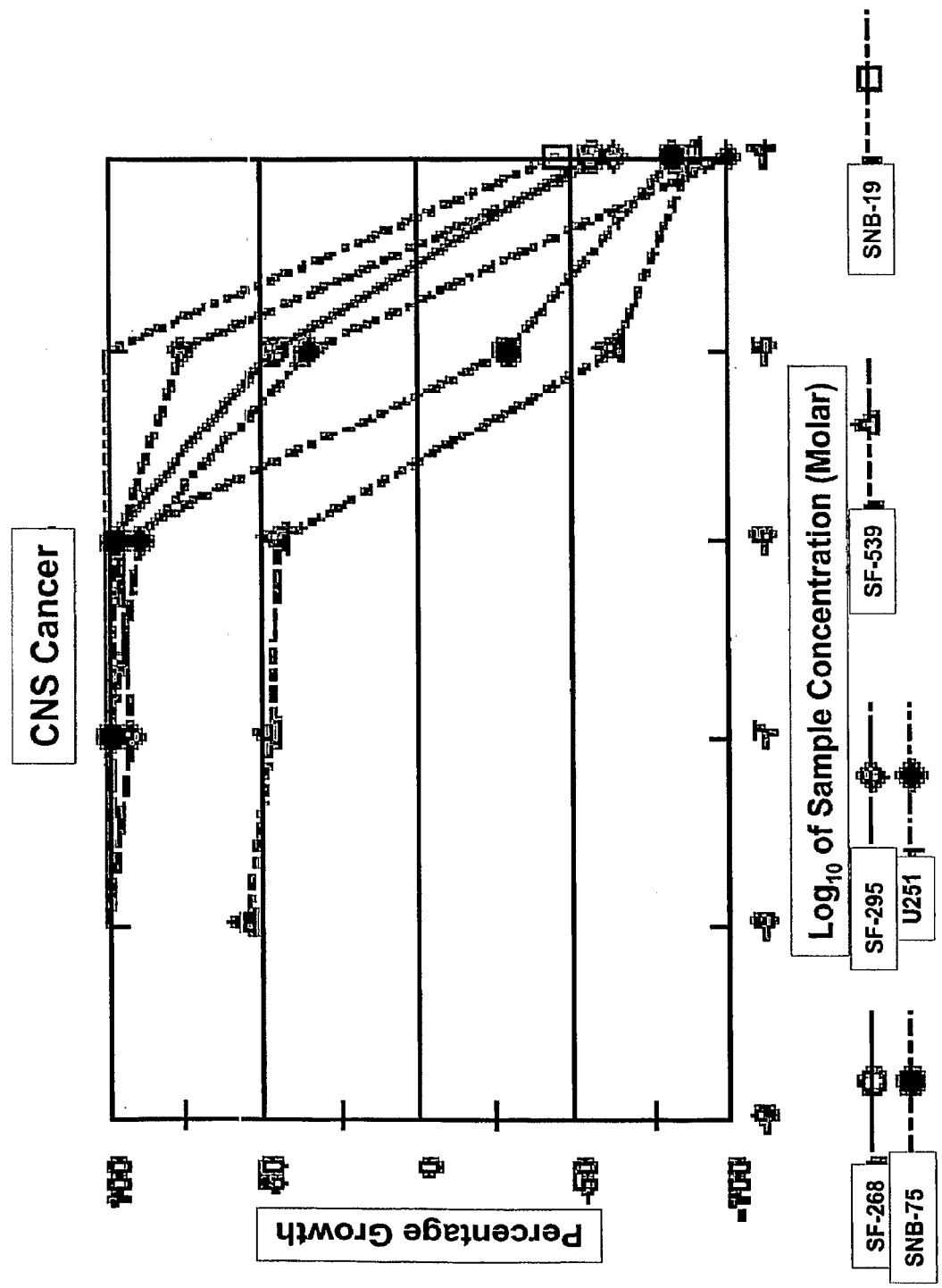
Figure 1E:
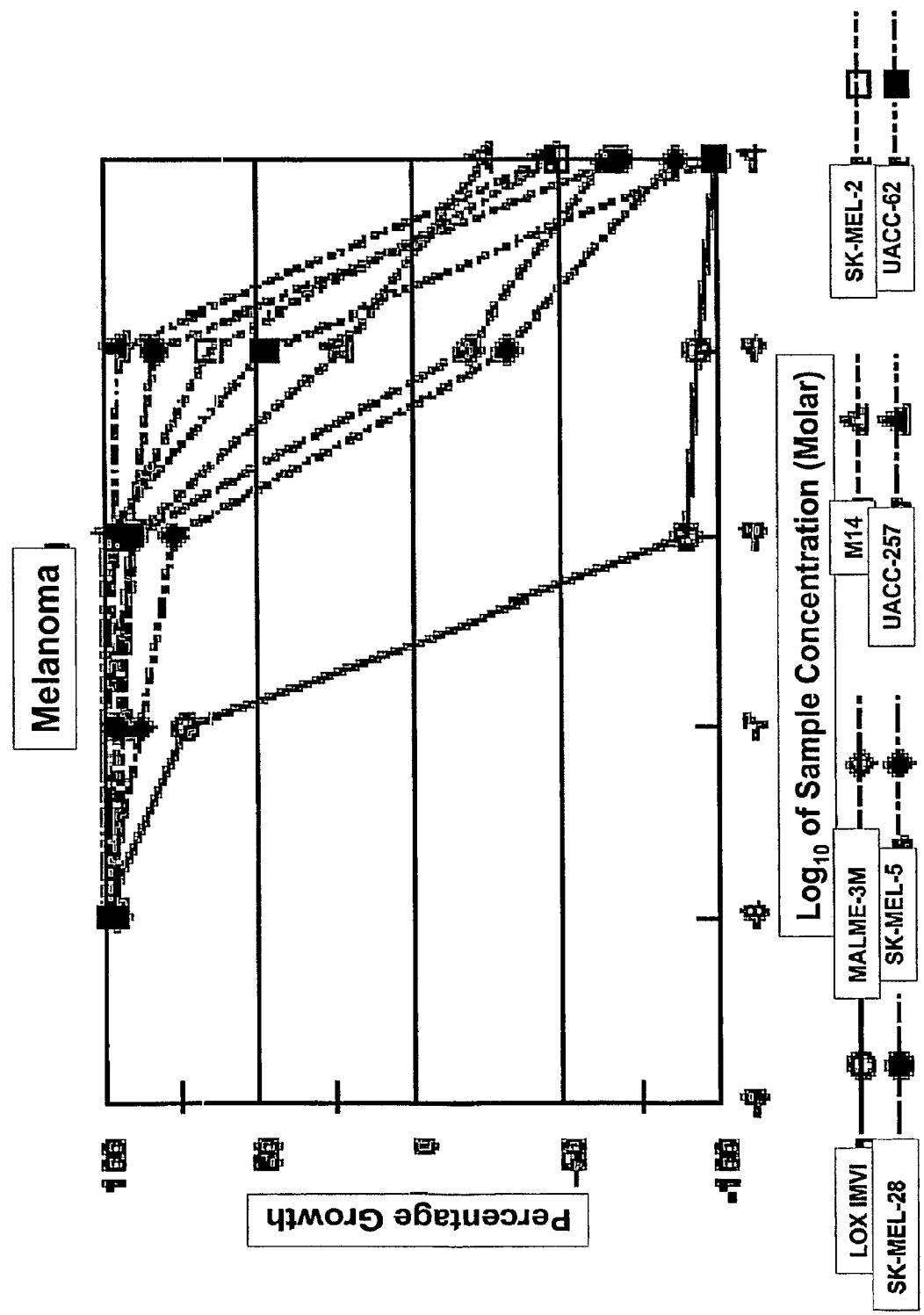
Figure 1F:
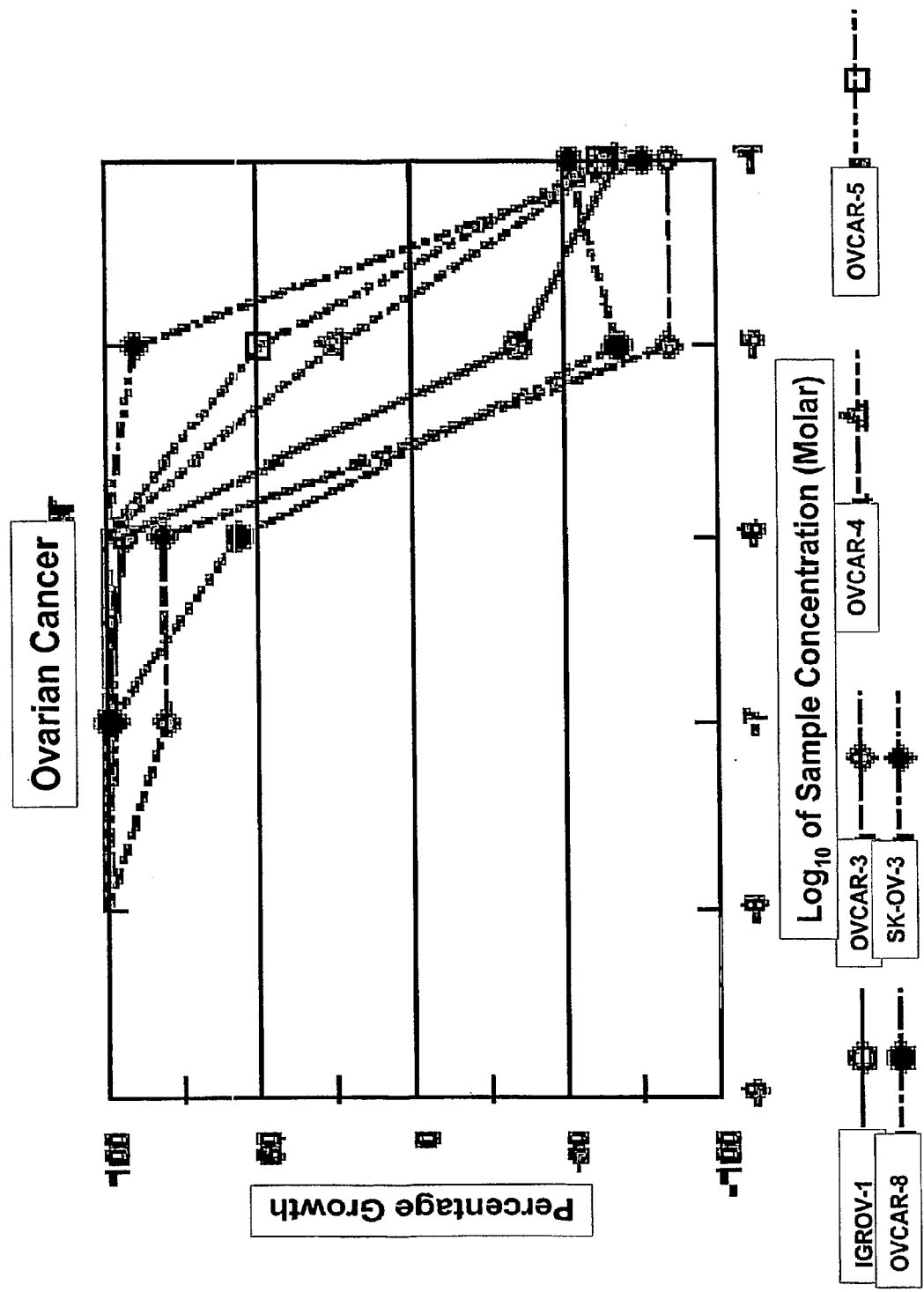
Figure 1G:
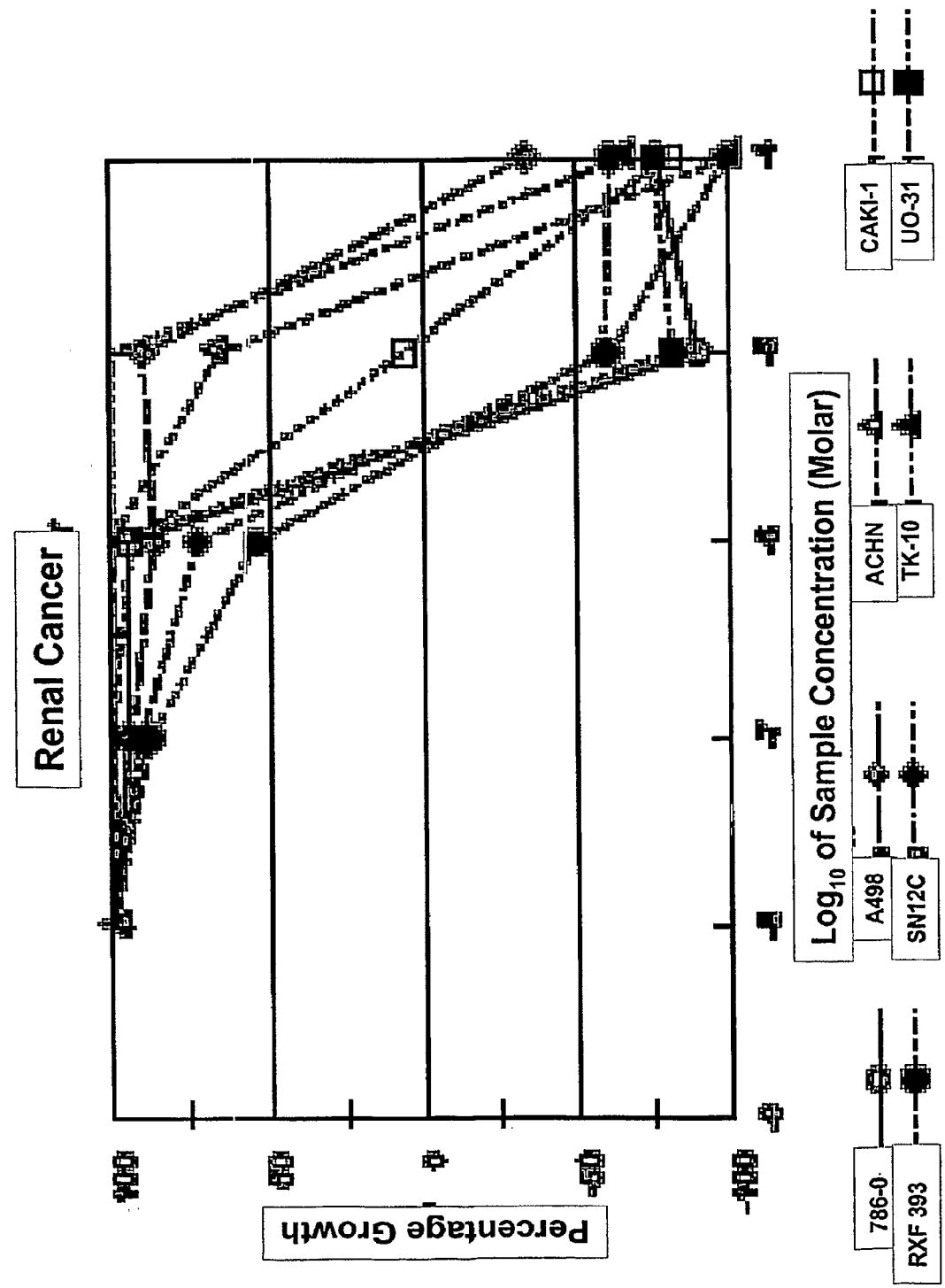
Figure 1H:
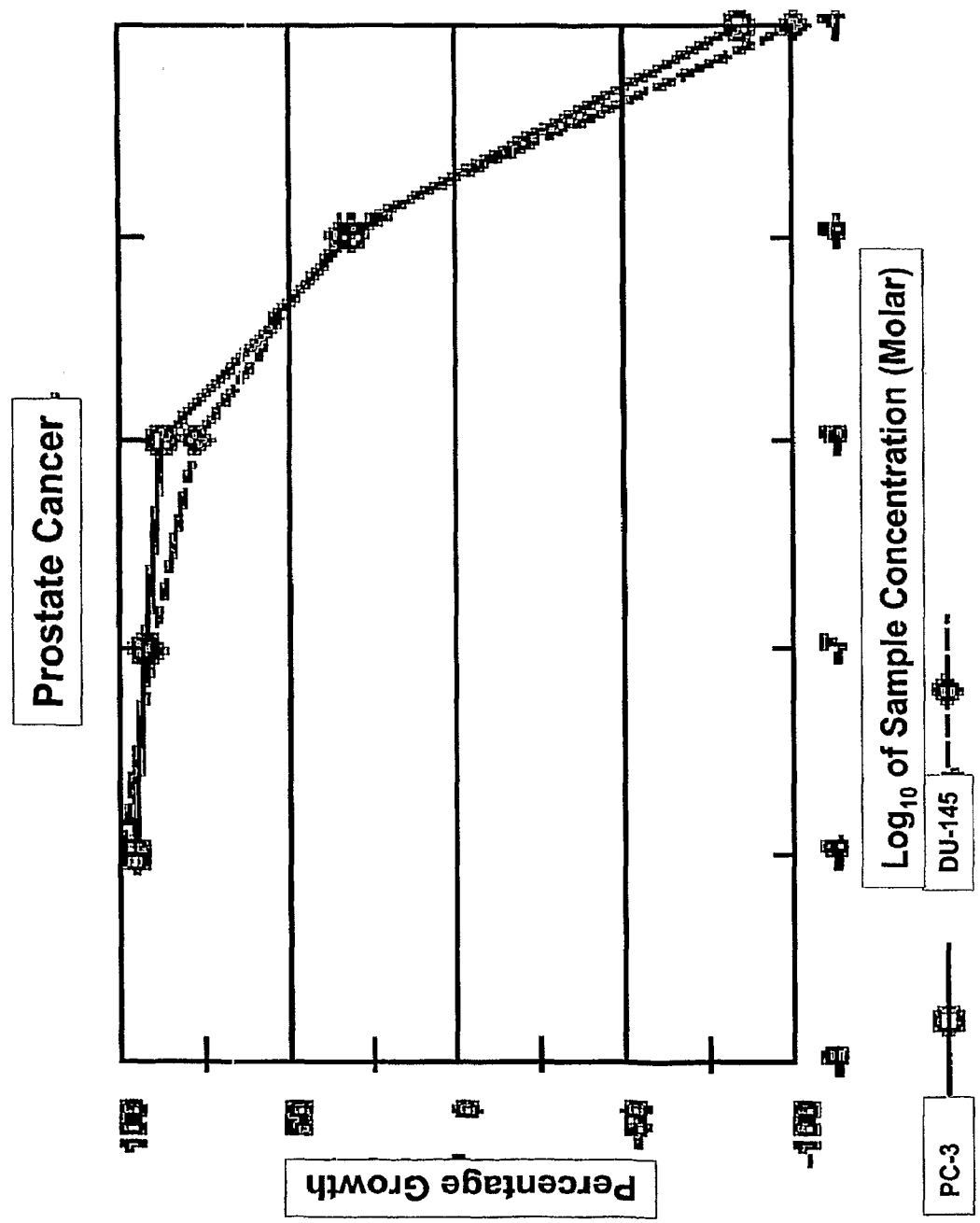
Figure 1I:
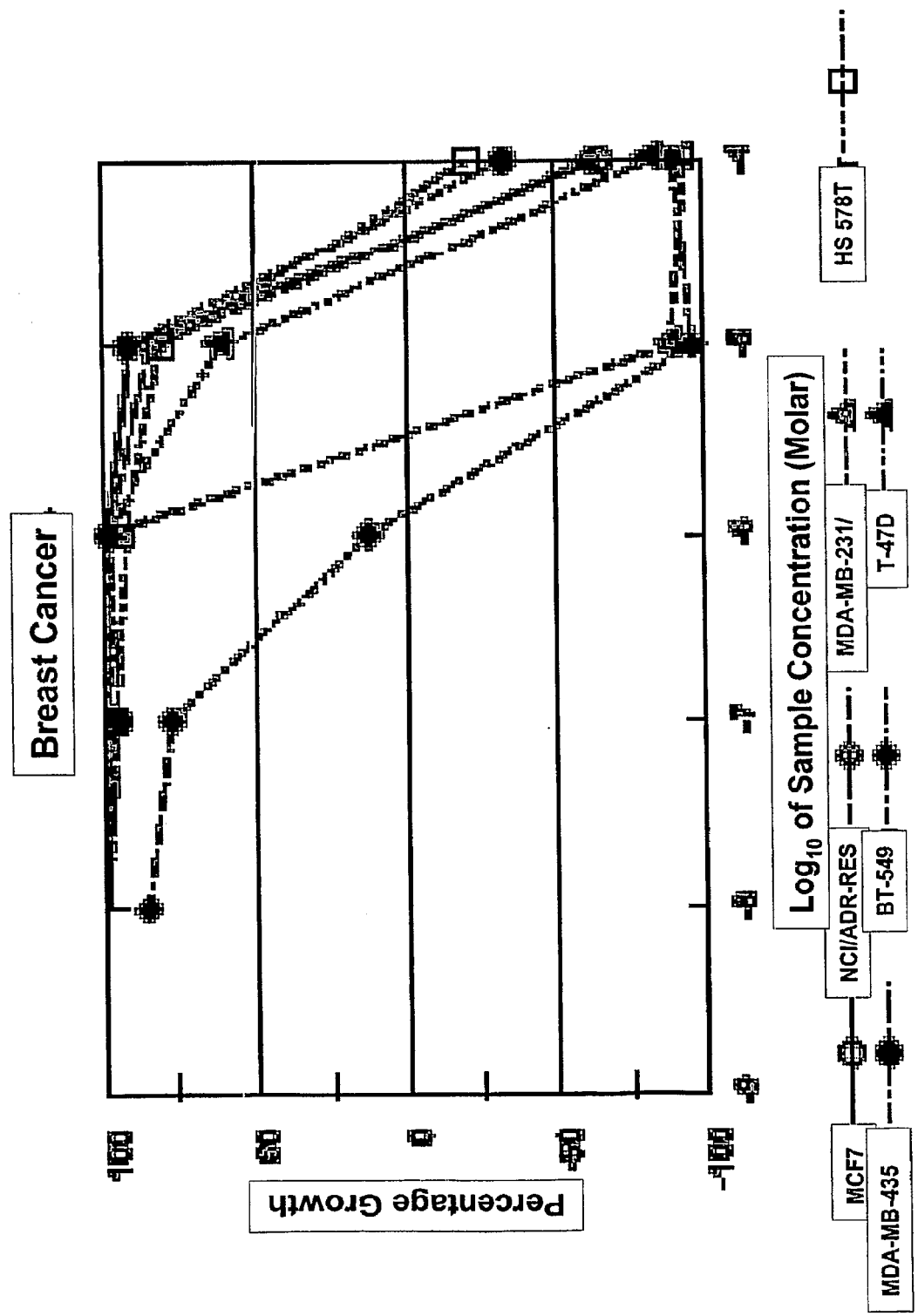
Figure 2A:
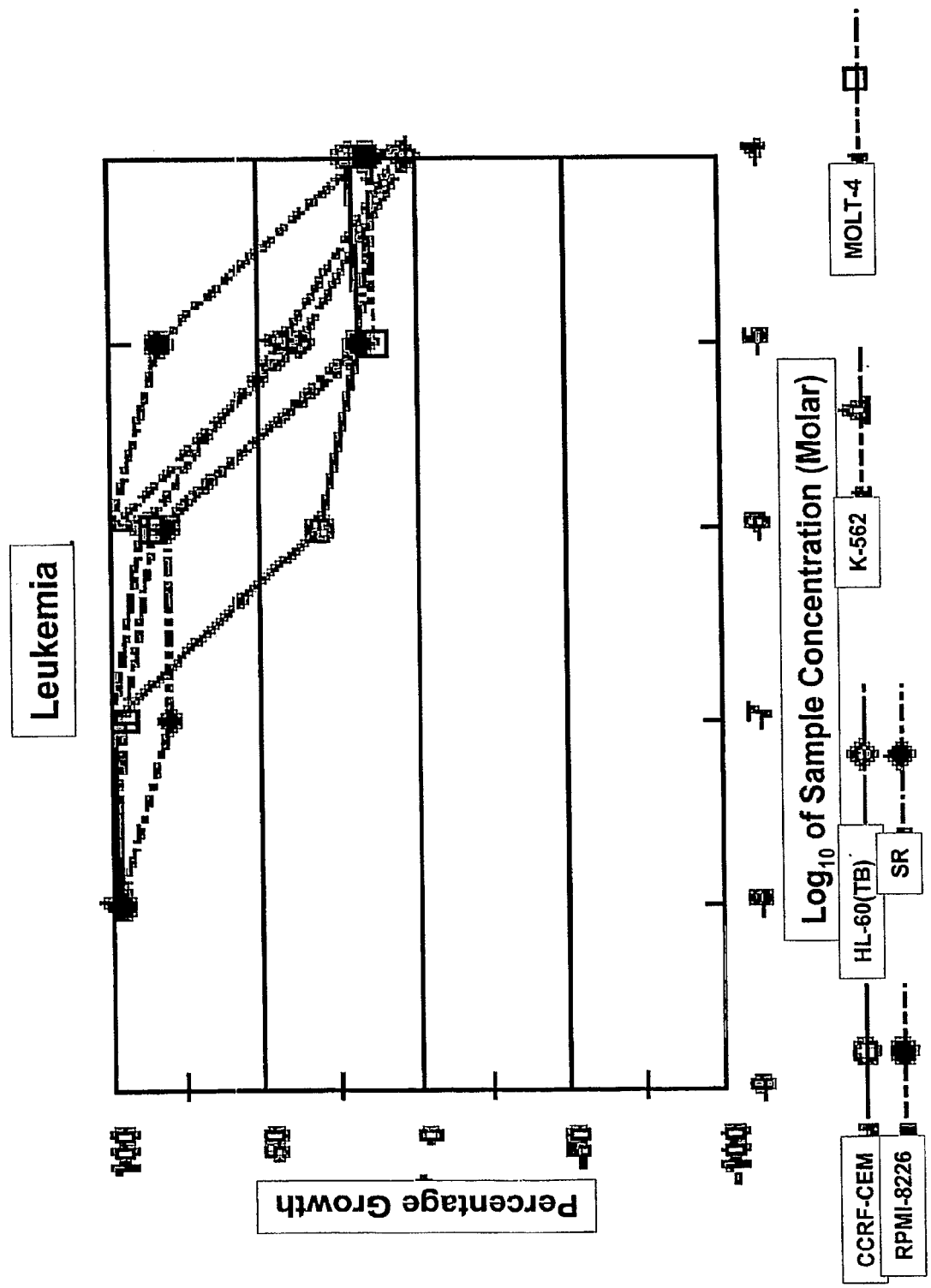
FIG. 2 (a) through (i). Represents graphs of the effect of HEVD analogs (Compound IX where R=phenyl and X=Br) on 60 cancer cell lines.
Figure 2B:
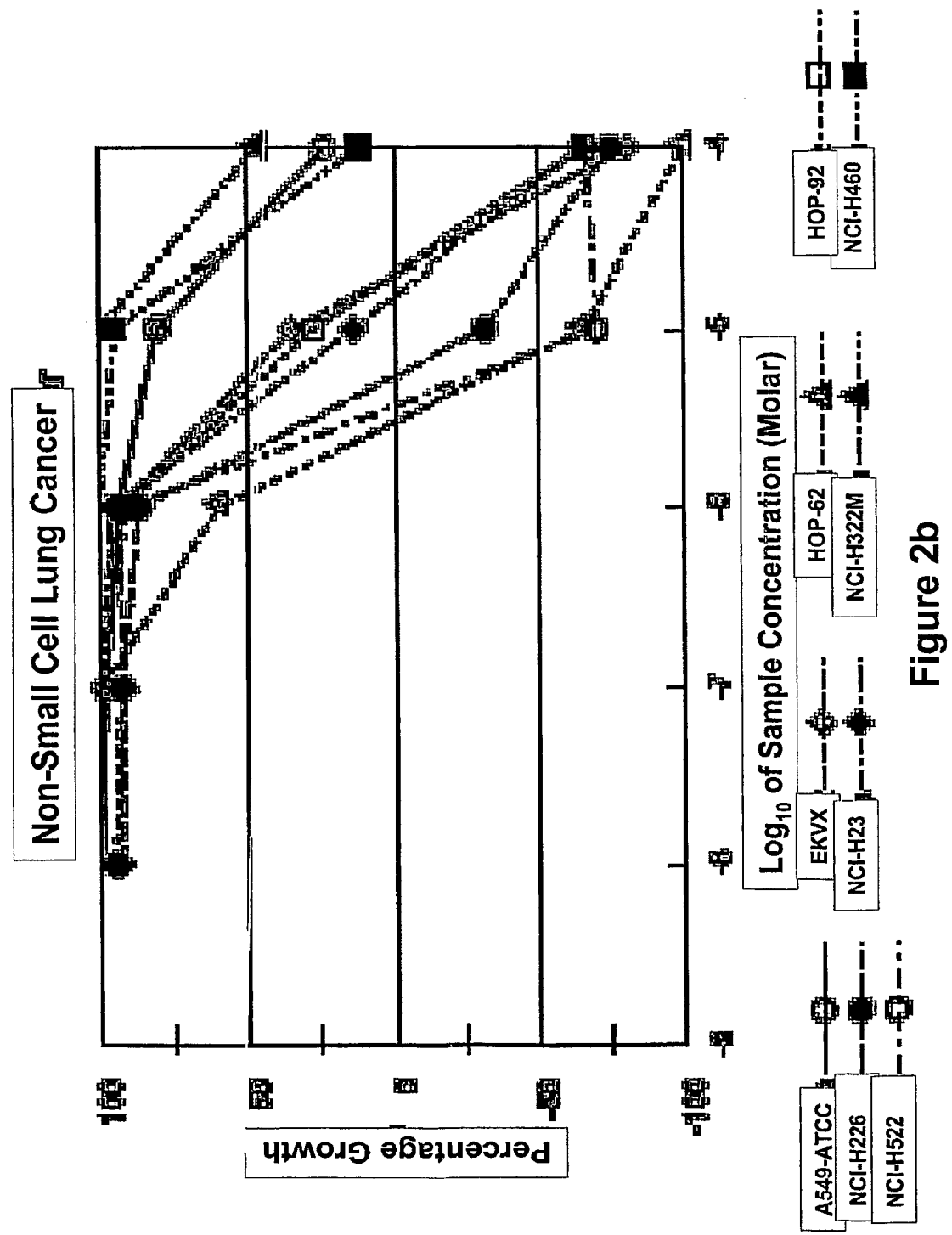
Figure 2C:
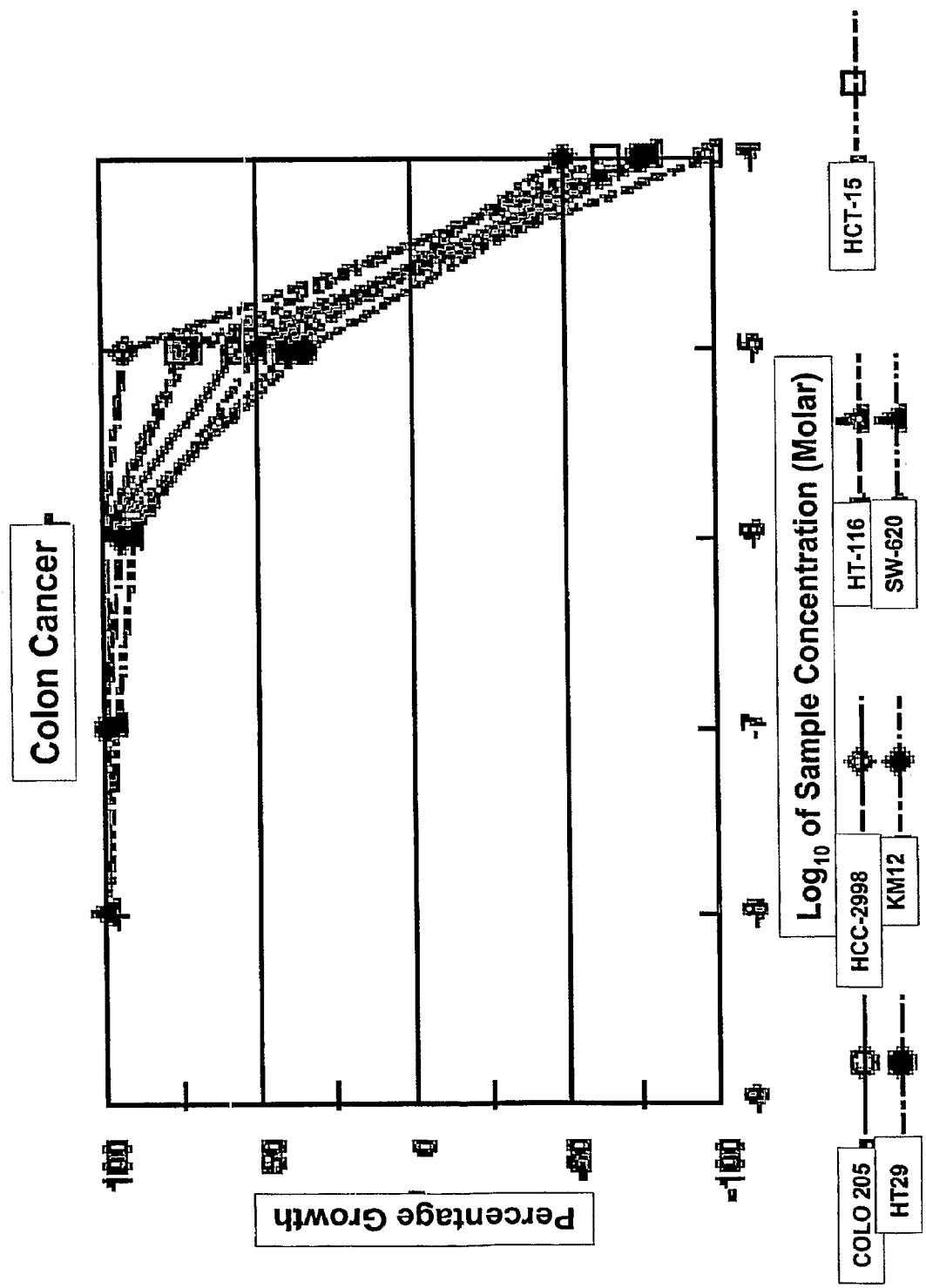
Figure 2D:
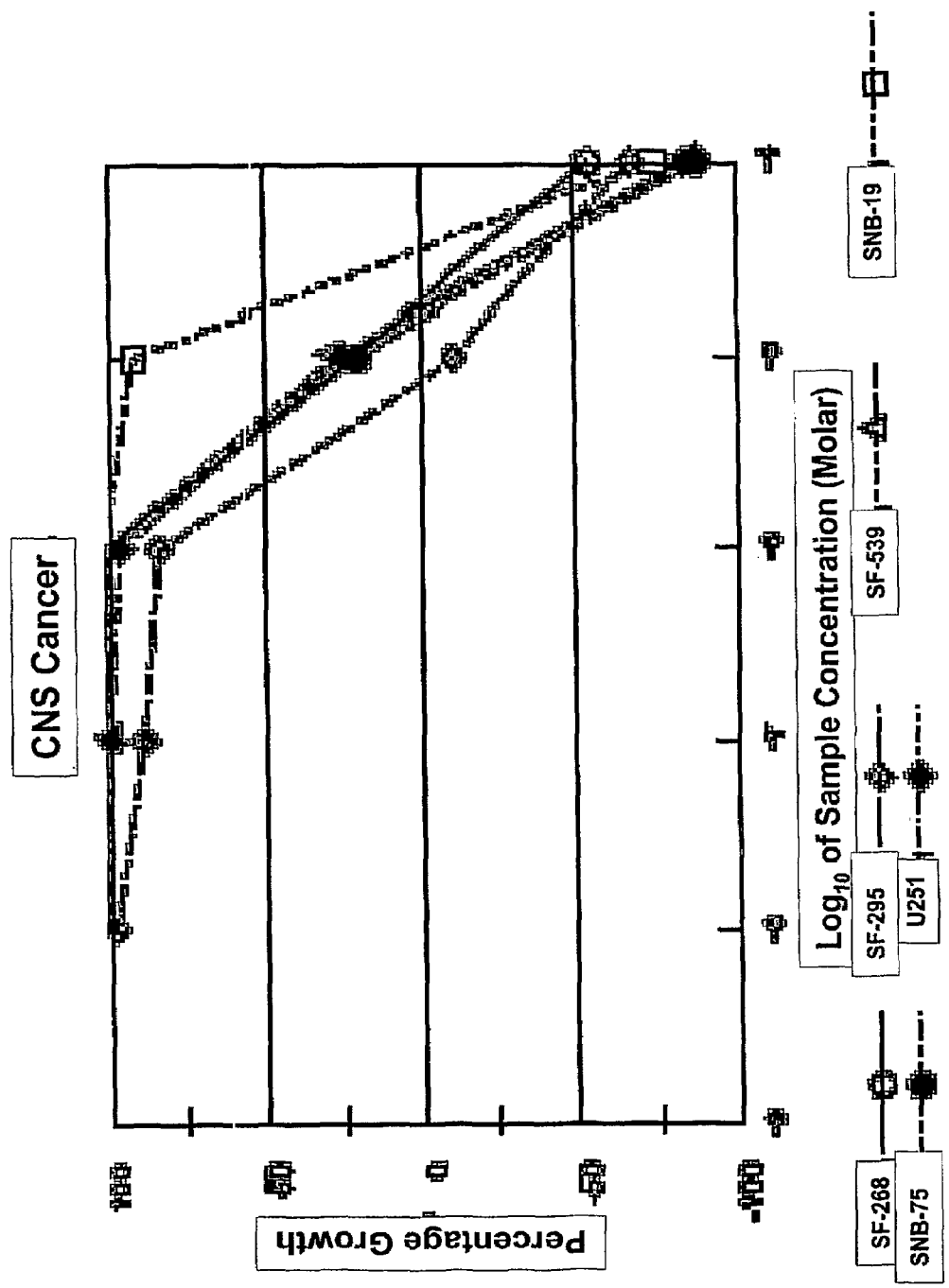
Figure 2E:
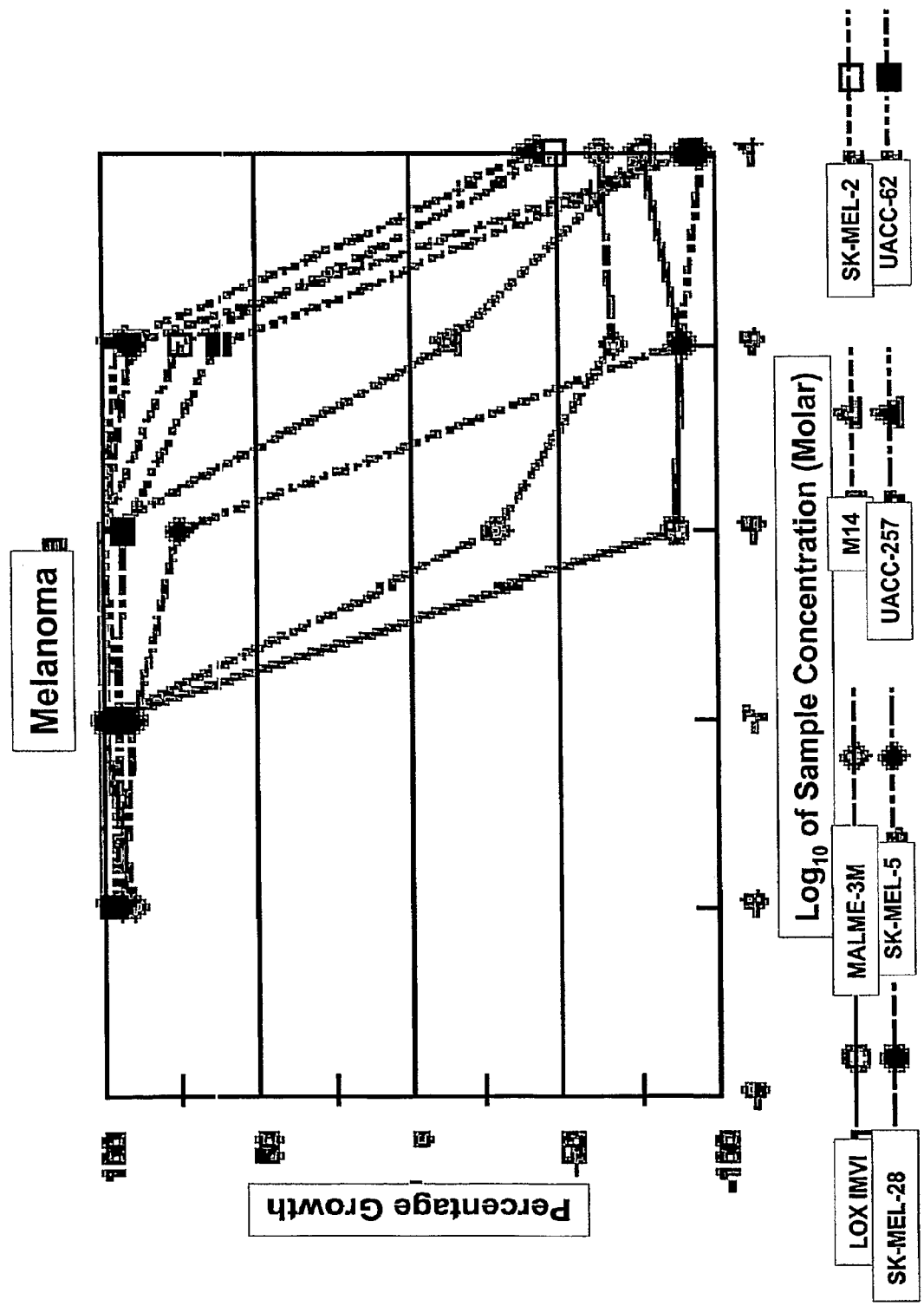
Figure 2F:
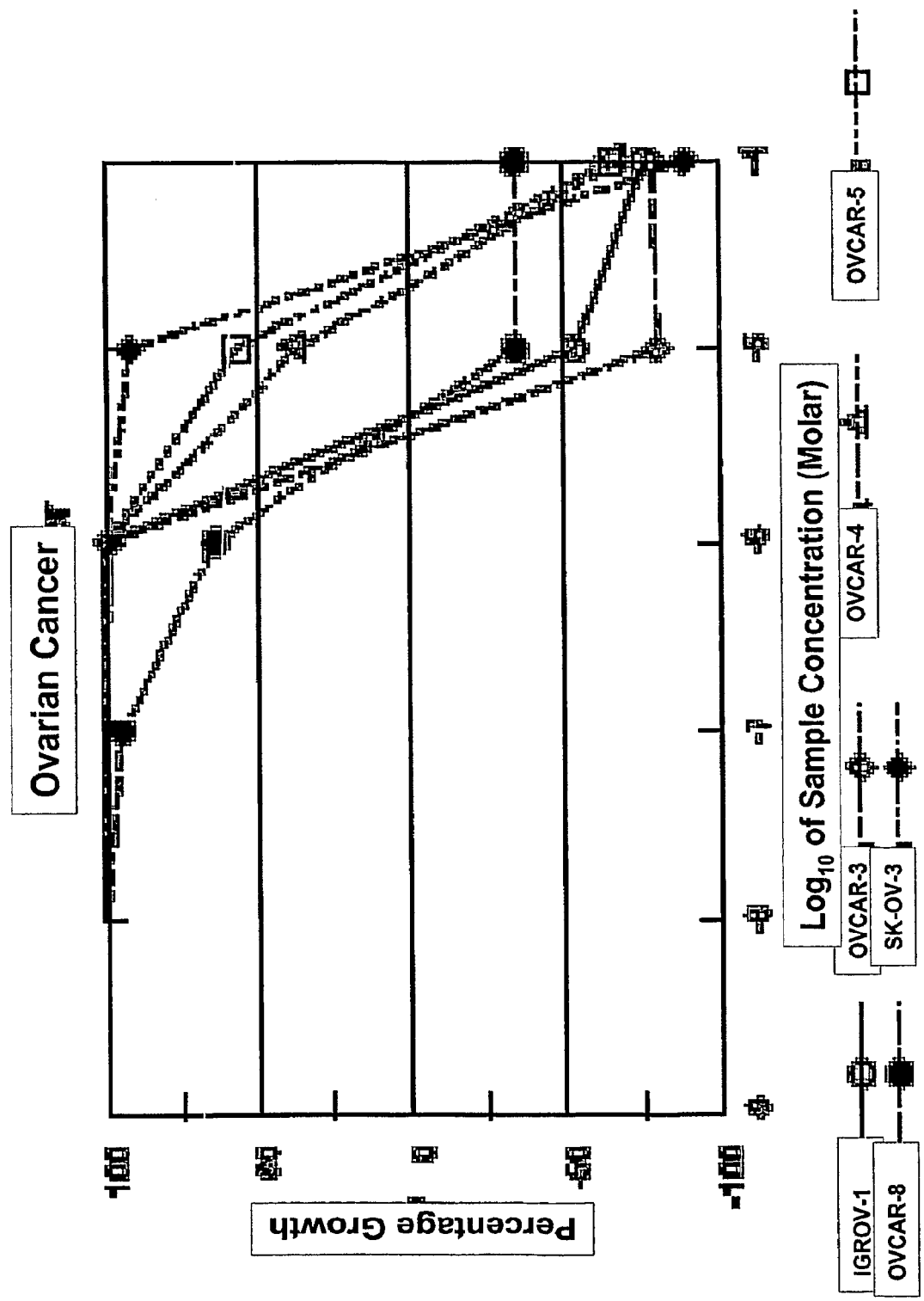
Figure 2G:
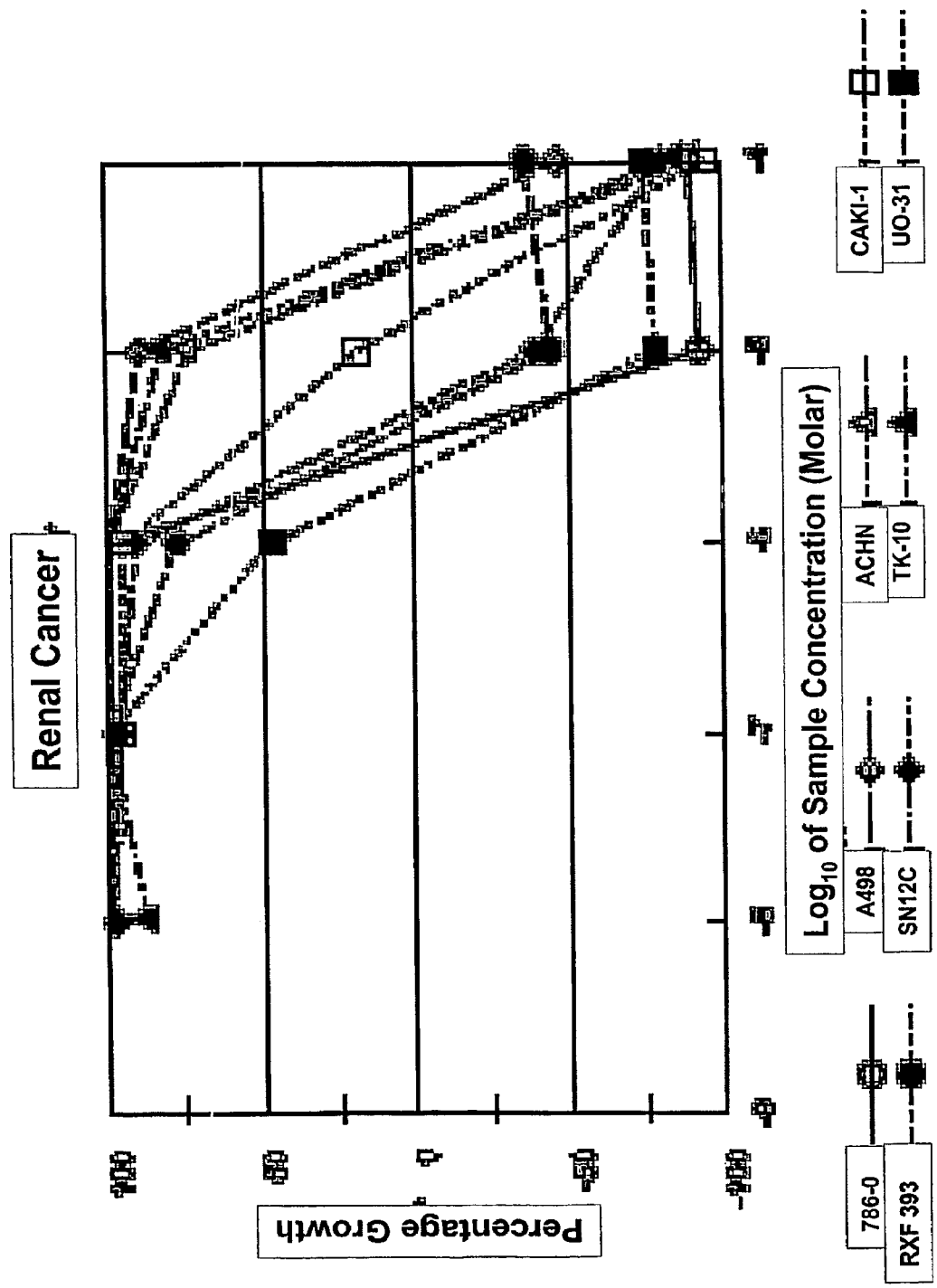
Figure 2H:
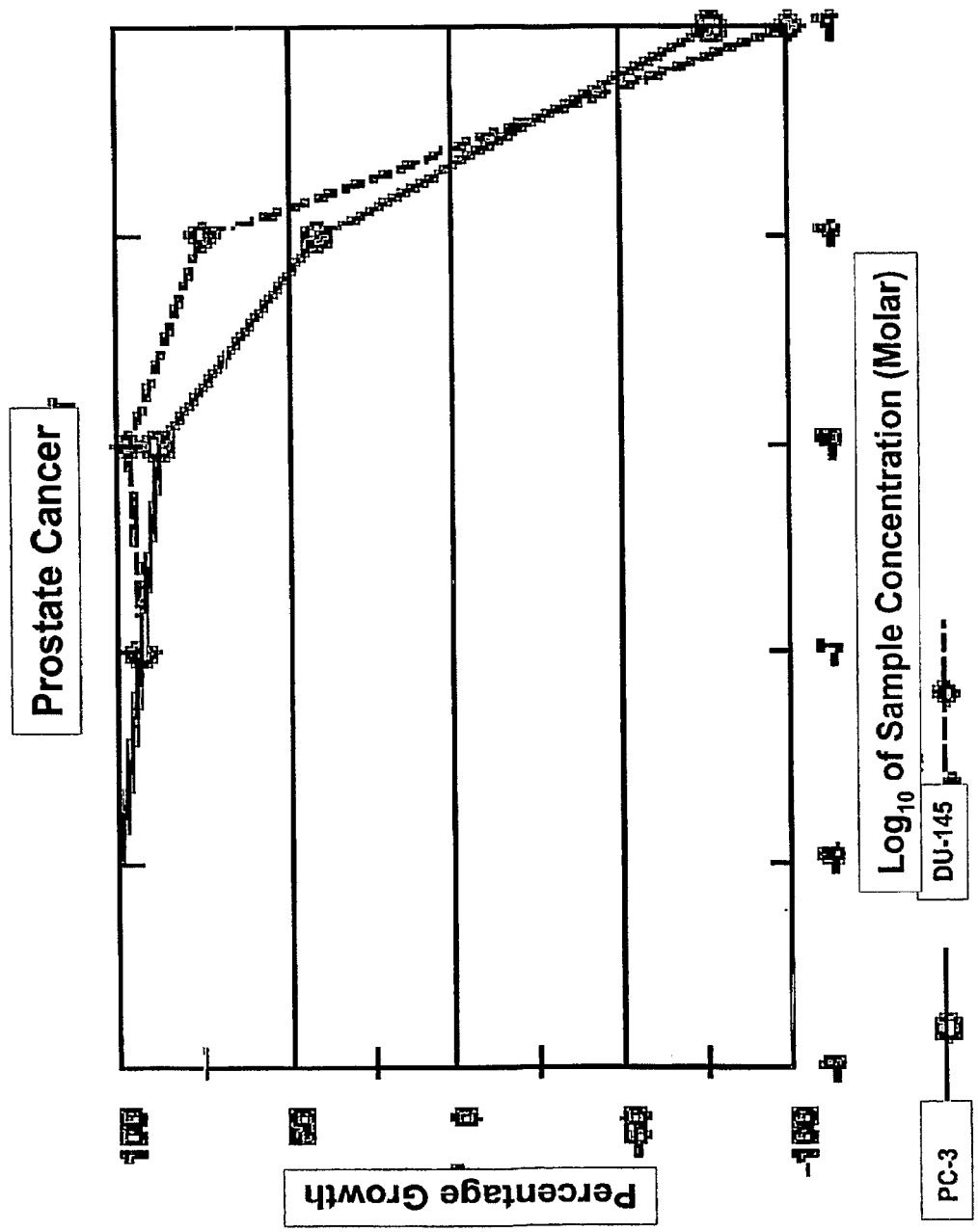
Figure 2I:
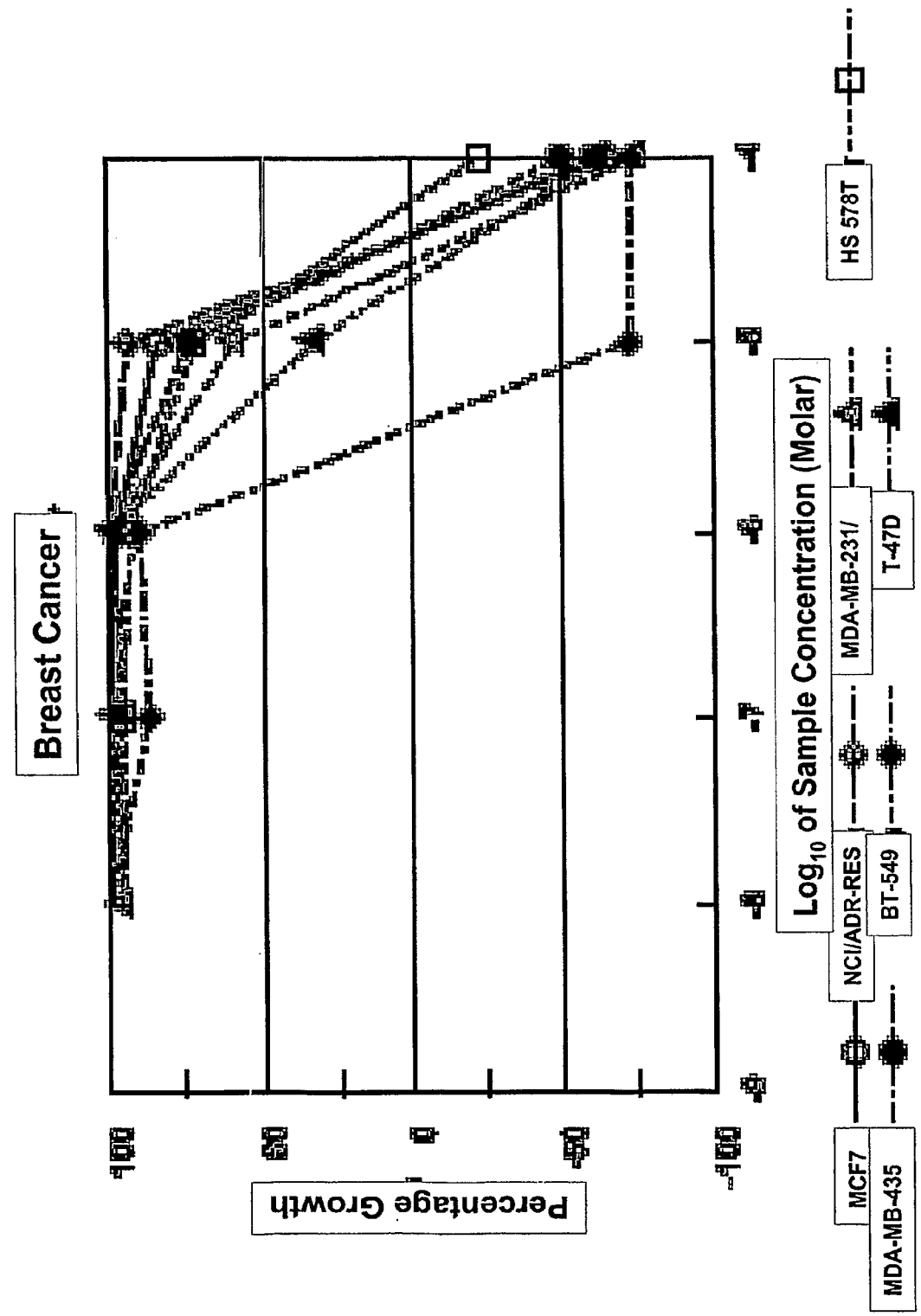

A class of heterocyclic derivatives of steroids such as ergocalciferol, calcidiol, calcitriol, cholecalciferol, cholesterol, ergosterol, analogs and derivatives that contain a conjugated diene system have been prepared in accordance with the invention. Similarly, other related derivatives obtained from molecular scaffolds that contain the typical conjugated diene or alkyne systems are also claimed to be within the scope of this invention. These heterocyclic derivatives exhibit anti-cancer, anti-proliferative activity, and anti-inflammatory, as well as general activity against other related disorders.

In one aspect, the invention comprises heterocyclic vitamin D analogs (HEVD) having therapeutic utility embodied by the following structures.

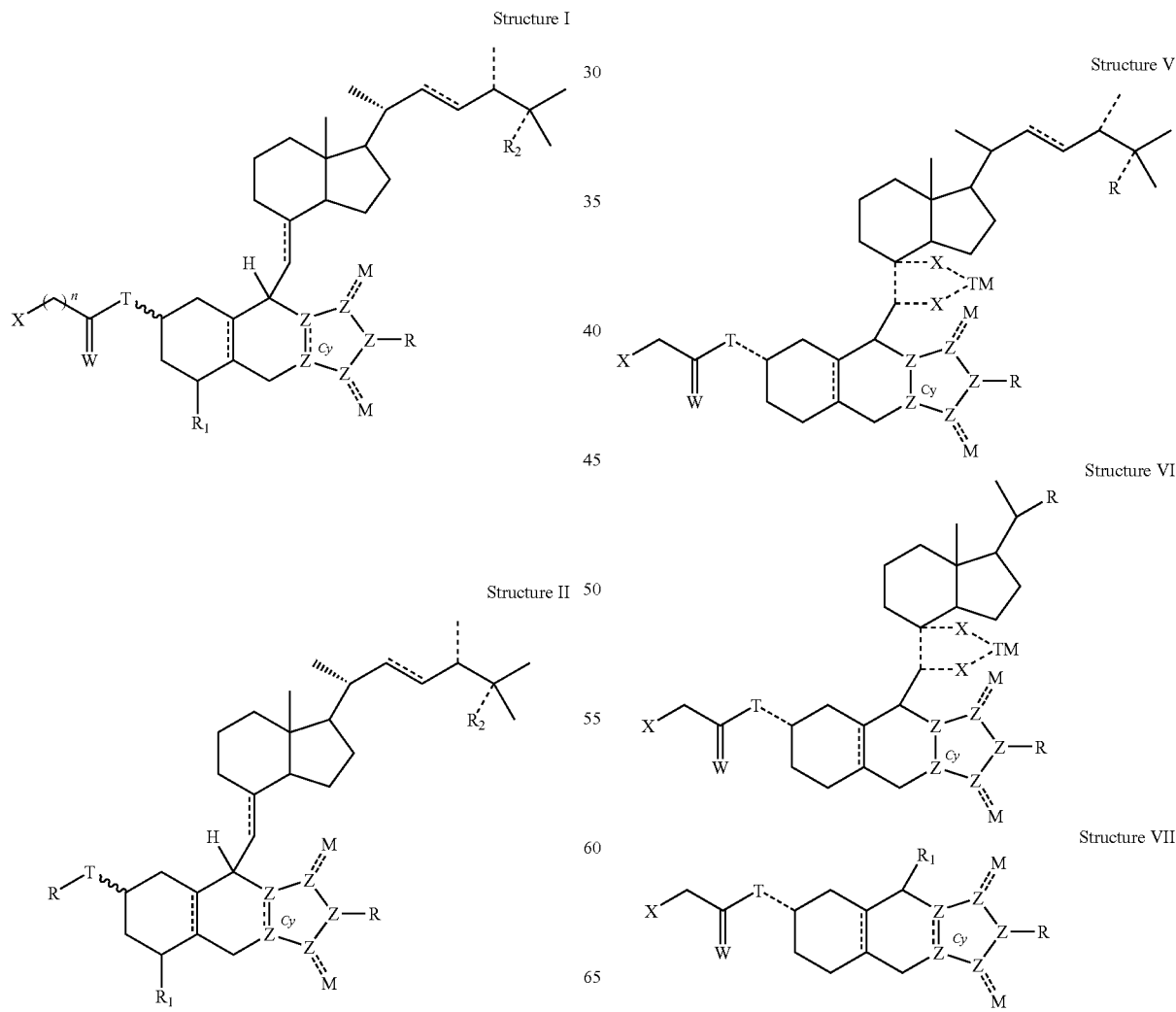

Where $R_5$ represents the side-chain in structure VIII as exemplified by but not limited to the drawings below.

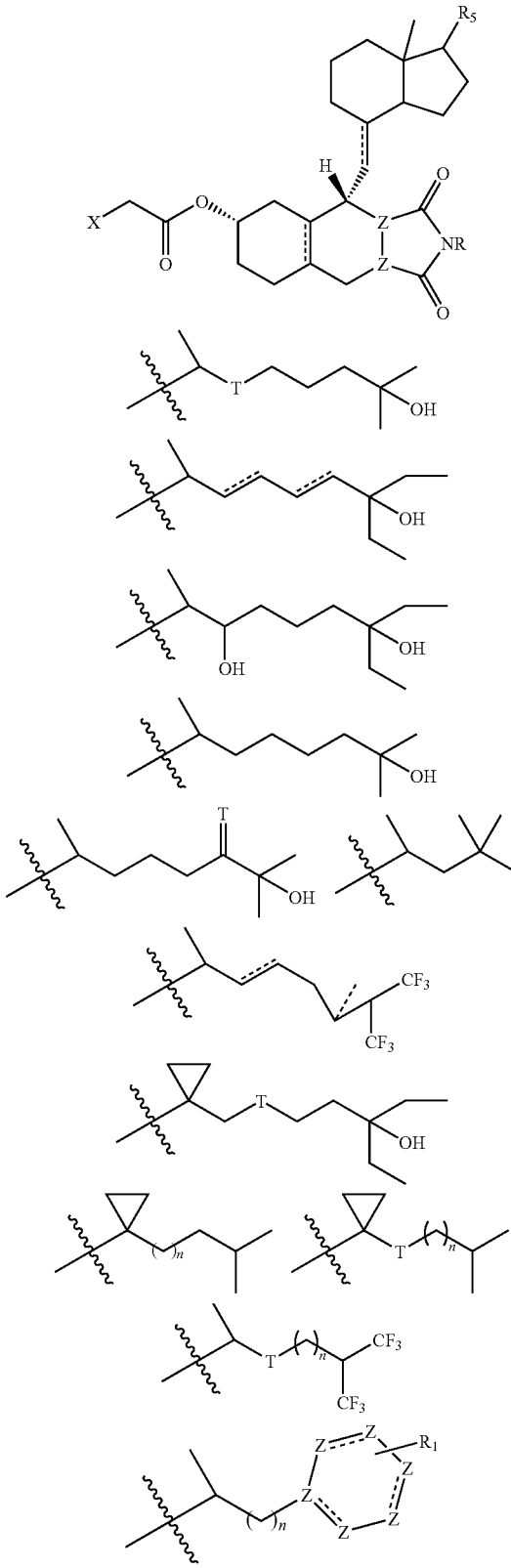

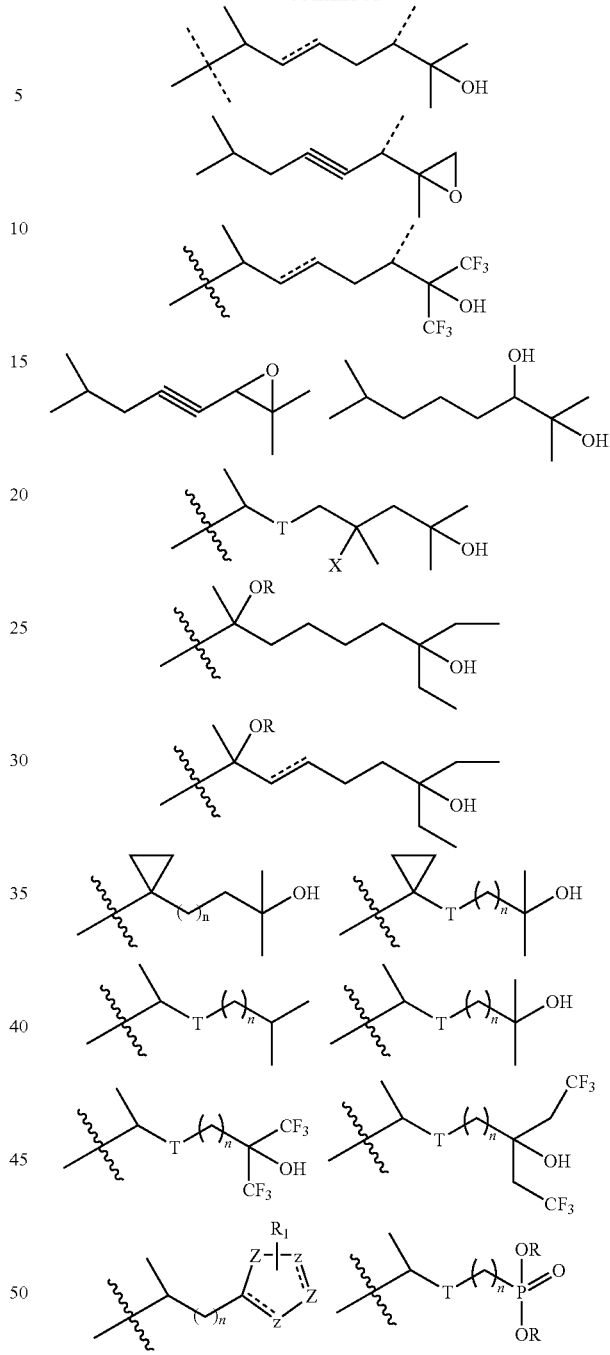

Where:
Z represents C or N
R represents atoms and groups as H, amino, hydroxyl, halogens and groups of atoms such as alkyl, aryl, heteroaryl, arylalkyl groups as defined below.
$R_1$ represents H, OH, OR, NH2, NR2, SH, SR and alkyl.
$R_2$ represents H, alkyl, alkenyl, alkynyl, aryl, heteroaryl, arylalkyl, heteroarylakyl, OH, COOH, COOR, COR, OR, SH, SR, SOR, $SO_2R$, CHO, halides, $NO_2$, $NH_2$, $NR_1R_2$, peptides, carbamoyl, thiocarbamoyl amides, ureas, thioureas, SO3H, SO3R, CN and derivatives as follows: tetrazoles and oxadiazoles.

The functionalities as mentioned herein can be further derivatized by those skilled in the art to afford the oximes, hydrazones and derivatives thereof, further such ring system can in isolated or in combined form can form a fused cyclic, bridged ring systems each further substituted with functionalities defined as in $R_1$ and $R_2$. Other ring systems such as bicyclic amines and diamines such as piperazine and piperidine, each functional groups further substituted with various other chemically modifiable functional groups. $R_2$ may additionally represent the various side chains and body of hormones or vitamins side chains such as vitamin D2, D3, vitamin A and seco-steroids and steroids.

A dashed line (----) represents a single, double and optical/stereo/geometrical bond isomers.

M represents C, S and N atoms in open and combined forms such as cyclic structures.

T represents O, C, N and S in single, double and suitable higher boded states as well.

TM is a transition metal. A transition metal is an element whose atom has an incomplete d sub-shell, or which can give rise to cations with an incompleted sub-shell." This definition corresponds to groups 3 to 11 on the periodic table.

W represents O, C, N and S and other functional groups such as $=CN$, $=CH-NO_2$, $=N-CN$, $=N-NO_2$ and include derivatives thereof, such as tetrazoles, thiazoles, oxadiazoles.

n represents number of carbon atoms or bio-isosteric replacements thereof. Note that a bioisostere is a compound resulting from the exchange of an atom or of a group of atoms with another, broadly similar, atom or group of atoms. The objective of a bioisosteric replacement is to create a new compound with similar biological properties to the parent compound. The bioisosteric replacement may be physico-chemically or topologically based, and Cy represents the ring size starting from 4 to 10 atoms, increasing to any size structurally allowable with the definition of Z as above, moreover such rings can be further substituted at any or every atom in the ring with such atoms and the groups defined in one and all of the above definitions.

Certain terms are defined in the follow manner:

The term "chiral" refers to molecules which have the property of non-superimposability of the mirror image partner, while the term "achiral" refers to molecules which are superimposable on their mirror image partner.

The term "stereoisomers" or "isomers" refer to compounds which have identical chemical constitution, but differ with regard to the arrangement of the atoms or groups in space. In particular, "enantiomers" refer to two stereoisomers of a compound which are non-superimposable mirror images of one another. An equimolar mixture of two enantiomers is called a "racemic mixture" or a "racemate".

"Diastereomers" refer to stereoisomers with two or more centers of dissymmetry and whose molecules are not mirror images of one another. With respect to the nomenclature of a chiral center, terms "d" and "l" configuration are as defined by the IUPAC Recommendations. As to the use of the terms, diastereomer, racemate, epimer and enantiomer will be used in their normal context to describe the stereochemistry of preparations.

The terms "isolated" or "substantially purified" as used interchangeably herein refer to HEVD compounds in a non-naturally occurring state. The compounds can be substantially free of cellular material or culture medium when naturally produced, or chemical precursors or other chemicals when chemically synthesized. In other preferred embodiments, the terms "isolated" or "substantially purified" also refer to preparations of a chiral compound which substantially lack one of the enantiomers, i.e., enantiomerically enriched or non-racemic preparations of a molecule. Similarly, isolated epimers or diasteromers refers to preparations of chiral compounds which are substantially free of other stereochemical forms.

As used herein, the language "alkyl" is art-recognized and includes to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl has 30 or fewer carbon atoms in its backbone (e.g., $C_1$-$C_{30}$ for straight chain, $C_3$-$C_{30}$ for branched chain), and more particularly 20 or fewer. Likewise, specific cycloalkyls have from 4-10 carbon atoms in their ring structure, and more specifically have 5, 6 or 7 carbons in the ring structure.

Unless the number of carbons is otherwise specified, "lower alkyl" as used herein means an alkyl group, as defined above, having from one to ten carbons. Attention is drawn to lower alkyls of from one to six, one to four carbon atoms in its backbone structure, which may be straight or branched-chain. Examples of lower alkyl groups include methyl, ethyl, n-propyl, i-propyl, tert.-butyl, hexyl, heptyl, octyl and so forth. Likewise, "lower alkenyl" and "lower alkynyl" have similar chain lengths to lower alkyls. Examples of alkylene groups are methylene, ethylene, propylene.

Moreover, the term alkyl as herein is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl (including aldehydes, ketones, carboxylates, and esters), alkoxyl, ether, phosphoryl, cyano, amino, acylamino, amido, amidino, imino, sulfhydryl, alkylthio, arylthio, thiolcarbonyl (including thiolformates, thiolcarboxylic acids, and thiolesters), sulfonyl, nitro, heterocyclyl, aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, acylaminos, iminos, amidos, phosphoryls (including phosphonates and phosphinates), sulfonyls (including sulfates, sulfonatos, sulfarnoyls, and sulfonamidos), and silyl groups, as well as ethers, alkylthios, arylthios, carbonyls (including ketones, aldehydes, carboxylates, and esters), $-CF_3$, $-CN$ and the like. Exemplary substituted alkyls are described below. Cycloalkyls can be further substituted with alkyls, alkenyls, alkoxys, alkylthios, arylthios, aminoalkyls, carbonyl-substituted alkyls, $-CF_3$, cyano ($-CN$), and the like.

The term "aralkyl", as used herein, refers to an alkyl group substituted with an aryl group (e.g., an aromatic or heteroaromatic group).

The terms "alkenyl" and "alkynyl" are art-recognized and include to unsaturated aliphatic groups analogous in length and possible substitution to the alkyls described above, but that contain at least one double or triple bond respectively.

The terms "alkoxyl" is art-recognized and includes to a group represented by the formula $-O$-alkyl. Representative alkoxyl groups include methoxy, ethoxy, propoxy, tert-butoxy and the like. Unless otherwise specified, an "alkoxy" group can be replaced with a group represented by $-O$-alkenyl, $-O$-alkynyl, $-O$-aryl (i.e., an aryloxy group), or $-O$-heterocyclyl. An "ether" is two substituted or unsubstituted hydrocarbons covalently linked by an oxygen. Accordingly, the substituent of, e.g., an alkyl that renders that alkyl an ether is or resembles an alkoxyl, such as can be represented by one of $-O$-alkyl, $-O$-alkenyl, $-O$-alkynyl, $-O$-aryl, or —O-heterocyclyl. The term "lower alkoxy" includes a lower alkyl group attached to the remainder of the molecule by oxygen.

Examples of alkoxy groups include methoxy, ethoxy, isopropoxy, and tert-butoxy. The term "phenyl alkoxy" refers to an alkoxy group which is substituted by a phenyl ring. Examples of phenyl alkoxy groups are benzyloxy, 2-phenylethoxy, 4-phenylbutoxy and so forth. The term "alkanoyloxy group" refers to the residue of an alkylcarboxylic acid formed by removal of the hydrogen from the hydroxyl portion of the carboxyl group. Examples of alkanoyloxy groups include formyloxy, acetoxy, butyryloxy, hexanolyoxy and so forth.

The term "substituted" as applied to "phenyl" refers to phenyl which is substituted with one or more of the following groups: alkyl, halogen ("X") (i.e., fluorine, chlorine, bromine or iodine), nitro, cyano, trifluoromethly and so forth.

The term "alkanol" or a "hydroxyalkyl" refer to a compound derived by protonation of the oxygen atom of an alkoxy group. Examples of alkanols include methanol, ethanol, 2-propanol, 2-methyl-2-propanol and the like.

As used herein the term "hydroxy-protecting group" includes any group which acts to the protection of hydroxy functional groups during subsequent reactions, including, for example, acyl or alkylsilyl groups such as trimethylsilyl, triethylsilyl, t-butyldimethylsilyl and analogous alkylated silyl radicals, or alkoxyalkyl groups such as methoxymethyl, ethoxymethyl, methoxyethoxymethyl, tetrahydrofuranyl or tetrahydropyranyl. A "protected-hydroxy" is a hydroxy function derivatized by one of the above hydroxy-protecting groupings.

As used herein, the term "halogen" designates —F, —Cl, —Br or —I; the term "sulfhydryl" or "thiol" means —SH; the term "hydroxyl" means —OH.

The term "aryl" is art-recognized and includes 5- and 6-membered single ring aromatic groups that may include from zero to four heteroatoms. Examples are benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, alkyl, aralkyl, alkenyl, alkynyl, cycloalkyl, hydroxyl, amino, acylamino, azido, nitro, sulfhydryl, imino, amido, amidino, phosphonate, phosphinate, carbonyl, carboxyl, silyl, ether, alkylthio, arylthio, sulfonyl, sulfonamido, sulfamoyl, ketone, aldehyde, ester, a heterocyclyl, an aromatic or heteroaromatic moiety, —CF$_3$, —CN, or the like. Aryl groups can also be fused or bridged with alicyclic or heterocyclic rings which are not aromatic so as to form a polycycle (e.g., tetralin).

The terms "heterocyclyl" or "heterocyclic group" are art-recognized and include 3- to 10-membered ring structures, more preferably 4- to 7-membered rings, which ring structures include one to four heteroatoms. Heterocyclyl groups include pyrrolidine, oxolane, thiolane, imidazole, oxazole, piperidine, piperazine, morpholine, lactones, lactams such as azetidinones and pyrrolidinones, lactones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, acylamino, nitro, sulfhydryl, imino, amido, phosphonate, phosphinate, carbonyl, carboxyl, silyl, ether, alkylthio, arylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and include two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, acylamino, nitro, sulfhydryl, imino, amido, phosphonate, phosphinate, carbonyl, carboxyl, silyl, ether, alkylthio, arylthio, sulfonyl, ketone, aldehyde, ester, a heterocyclyl, an aromatic or heteroaromatic moiety, —CF$_3$, —CN, or the like.

In some embodiments, the groups described above may be substituted with following classes of special groups such as amino acids (optically active, both antipodes, racemic, unnatural amino acids), peptides (open or cyclic) containing all coded and uncoded amino acids (as described in literature) in single or in multiple repeating units such as polypeptides, sugars including monomers and repeated units thereof and other classes of molecules that may be categorized as biologicals and other natural products such as for example hormones and vitamins.

These compositions of this invention may be employed to modulate the physical and/or pharmaceutical aspects of other drugable compositions including existing, experimental or orphan drugs, nutraceutical, cosmeceuticals or pro-drugs either alone or in any combination therapy for use in animals and humans. Such physical and/or pharmaceutical aspects include (but are not limited to) solubility, stability, pharmacokinetic and pharmacodynamic profiles.

Some of the scaffolds described below represent the body of the broad scope of the present invention.

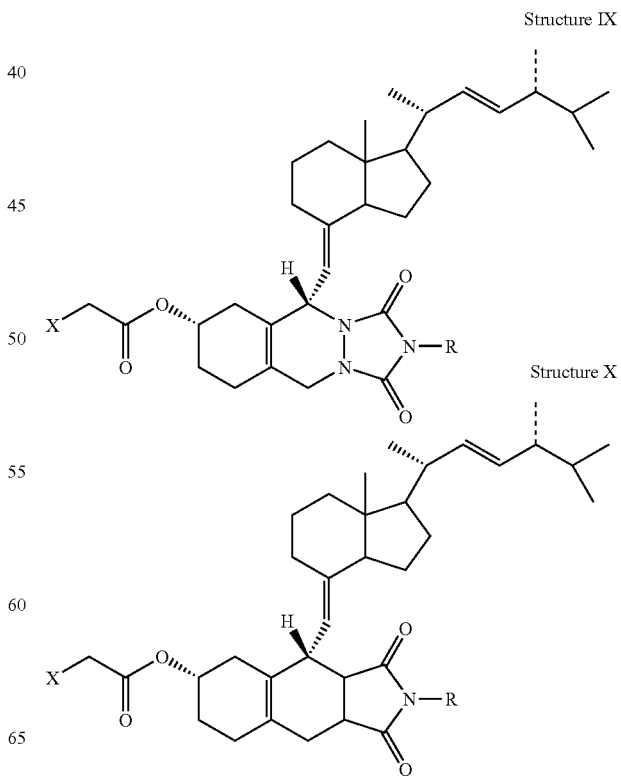

Structure IX

Structure X

Structure XI
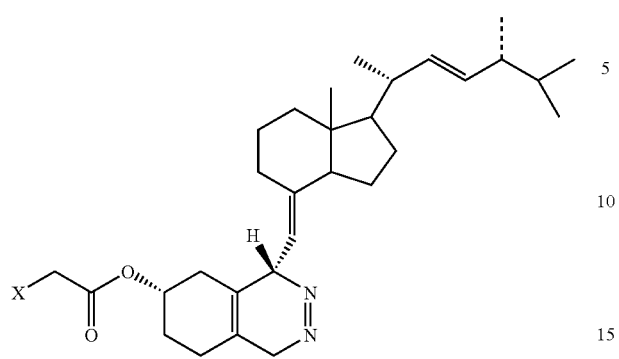
Structure XII
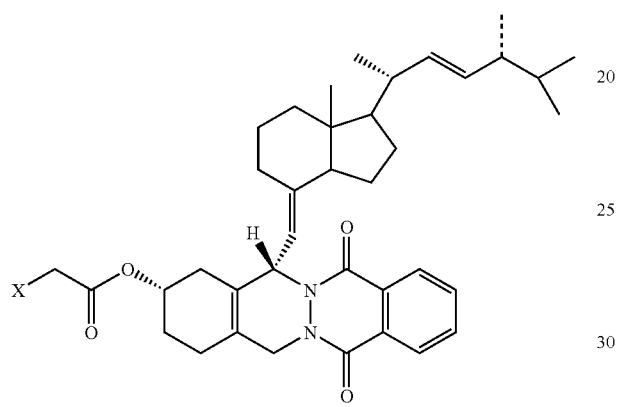
Structure XIII
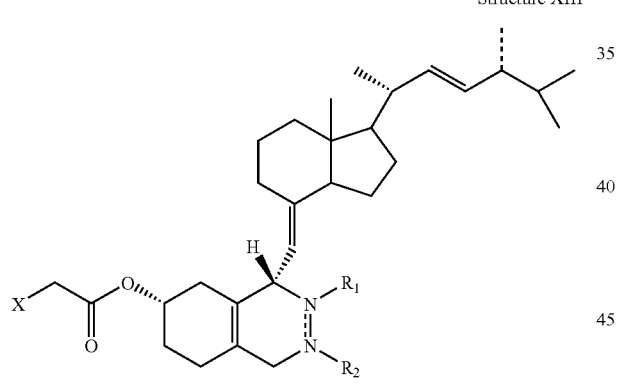
Particular note is made of the following compositions.
Structure XIV
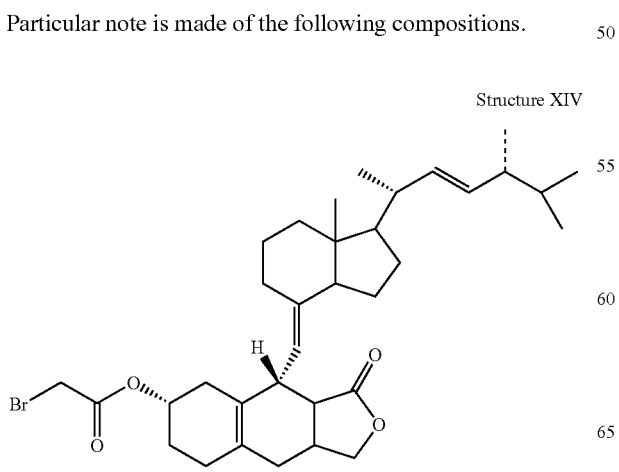
Structure XV
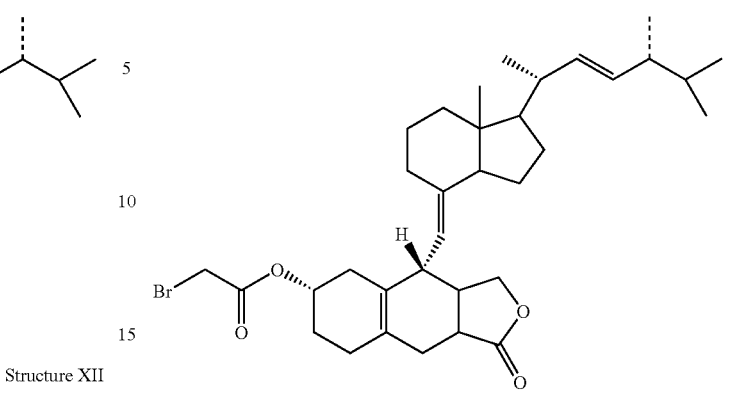
Structure XVI
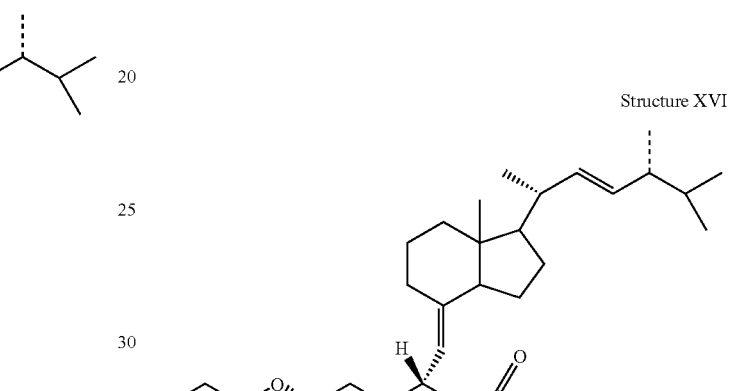
Structure XVII
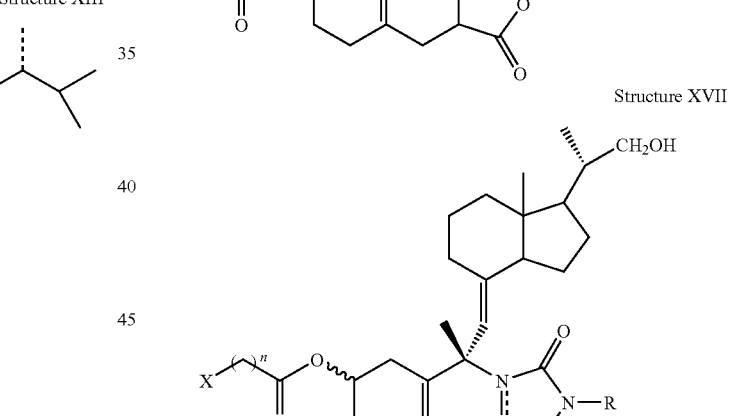
Structure XVIII
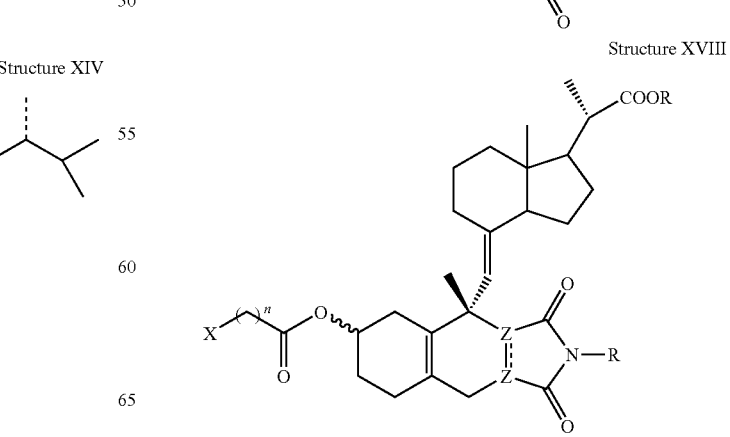

-continued

Structure XIX

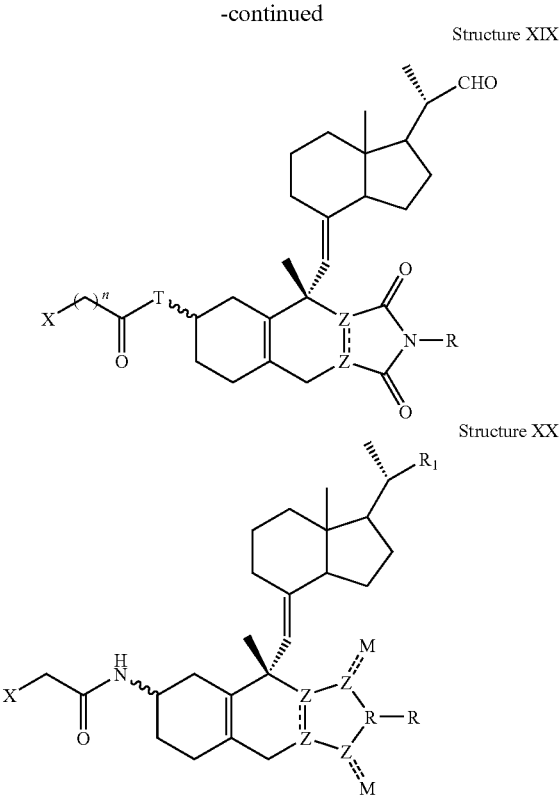

Structure XX

-continued

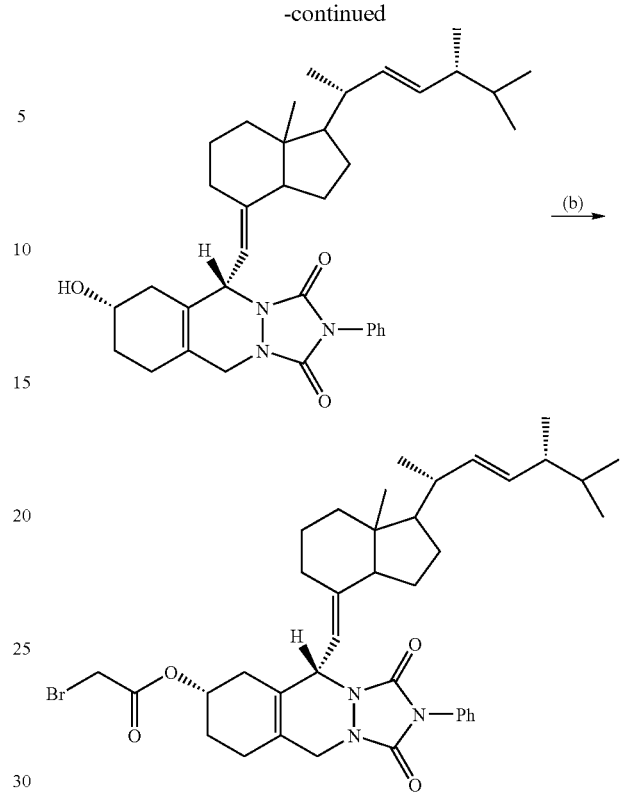

Reagent and Conditions: (a) 4-phenyl-1,2,4-triazoline,-3,5-dione, EtOAc, Ar, 0° C., 1-12 hrs; (b): Bromoacetic acid, 1,3-dicyclohexyl-carbodiimide (DCC), Dimethylaminopyridine (DMAP), Pyridine, DCM, 0° C., 1-12 hrs.

Yet another aspect of this invention comprises a method of synthesizing HEVD analogs, as exemplified by the reaction described in Scheme 1. Those skilled in the art should appreciate that these molecules and the analogs thereof can be synthesized in more than one way Ls exemplified by the reaction described in Scheme 1, by varying reactions conditions, using different solvents or combinations of solvents or media, by using different inert gases or catalysis in order to change the dynamics of the reaction, to create the bias towards a preferred isomer or polymorph, optical active isomers and a mixtures thereof. In particular all such methods leading to synthesis, isolation, purification in the various polymorphic, isomeric, diastereo-isomeric, racemic and geometrical or regio-isomers and racemic form and a mixtures and combinations thereof clearly form the body and claim of this invention.

The HEVD analogs of the invention may be used alone or in combination with known chemotherapeutic agents in the treatment of proliferative, angiogenic or inflammatory disorders and conditions requiring an anti-proliferative, anti-angiogenic, vascular disrupting and/or anti-inflammatory agent. Examples of such conditions or disorders include human solid tumors, such as but not limited to, gynecological solid tumors, prostate cancer, neuroblastoma, breast cancer, thoracic solid tumors, gastrointestinal solid tumors (for example, solid tumors of the liver, pancreas, and large/small bowel), psoriasis, rheumatoid arthritis, inflammatory bowel disease, scleroderma, Guillain-Barre syndrome, epilepsy, multiple sclerosis, polyarteritis nodosa and esophagitis for example. The heterocyclic steroid derivatives called herein as HEVD and described above are also be employed alone or in combination with the therapies for the treatment of infection as antimicrobial, antifungal or antibacterial agents.

Yet another aspect of the invention comprises the therapeutic compositions for treating the disorders and conditions described above. Such compositions comprise therapeutically effective amounts of one or more HEVD analogs of the invention in admixture with a pharmaceutically acceptable carrier. These compositions can be systemically administered either parenterally, intravenously, intramuscularly or subcutaneously. Alternatively, the compositions can be nasally, sublingually, transdermally, topically or orally administered. When systemically administered the therapeutic compositions for use in this invention are, of course, in the form of a pyrogen-free, parenterally acceptable aqueous solution. The preparation of such solutions having due regard to pH, isotonicity, stability and the like is within the level of skill in the art.

Scheme 1.

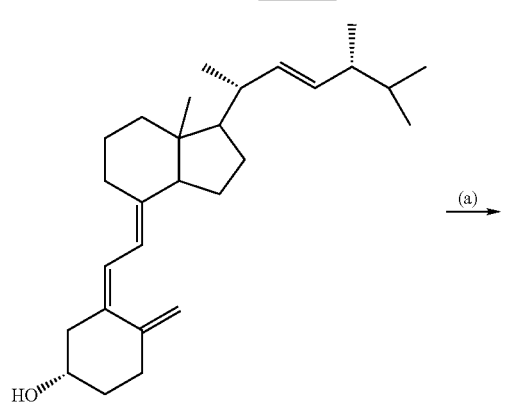

See; *Remington: The Science and Practice of Pharmacy*, Ed. Randy Hendrickson, Lippincott, Williams & Wilkins, 21$^{st}$ Edition (2005), the teachings of which are incorporated by reference.

Yet another aspect of the invention comprises all metabolites of HEVD analogs produced in organisms such as humans, rodents, bacteria and all other bioengineered cells or animals, which we contemplate isolating and evaluating for their therapeutic potentials, alone, or in combination with the parent molecules or in combination with any other therapeutic agents in the form of therapy and delivery currently or to be used in the future. Their synthetic analogs shall be understood to be falling within the scope and body of this invention as well.

The dosage regimen will be determined by the attending physician considering various factors that modify the action of pharmaceuticals, for example, the conditions, body weight, sex and diet of the patient, the severity of conditions and the presence of other diseases and/or conditions, the time of administration and other clinical factors known to those of skill in the art. Generally, the daily regimen should be in the nanogram to microgram range for most conditions and diseases, in the microgram to milligram range for those conditions and diseases caused by fungal, bacterial or other infectious diseases. For example, in unit dosage form an effective or therapeutic amount of a heterocyclic vitamin D analog of the invention is about 0.01 ng/kg/day to about 30 mg/kg/day, preferably about 0.1-3 mg/kg/day.

It should, of course, be understood that the methods of this invention can be used in combination with other agents. It is possible to administer the active ingredient of this invention as a single active pharmaceutical agent and pharmaceutical salts thereof, and also as part of a pharmaceutical formulation. The pharmaceutically acceptable formulations of the present invention comprise at least one compound of this invention in a therapeutically or pharmaceutically effective dose and pharmaceutical salts thereof, together with, optionally, one or more pharmaceutically or therapeutically acceptable carriers and optionally other therapeutic ingredients. Carriers include inert, non-toxic solids (e.g., mannitol, talc) and buffered saline. Various considerations are described in, for example, *Goodman and Gilman's: The Pharmacological Bases of Therapeutics*, Eds. Laurence Brunton, John Lazo, Keith Parker 11th Ed., Pergamon Press (2005); and Remington's infra, each of which is hereby incorporated herein by reference. Methods for administration are discussed therein, e.g., for oral, intravenous, intraperitoneal, or intramuscular administration, and others. Pharmaceutically acceptable carriers will include water, saline, buffers, and other compounds described in a number of sources including the *Merck Index*, Merck & Co., Rahway, N.J., incorporated herein by reference. As used herein, the term "pharmaceutically acceptable carrier" encompasses any of the standard pharmaceutical carriers such as sterile solutions, tablets, coated tablets, and capsules. Typically such carriers contain excipients such as starch, milk, sugar, certain types of clay, gelatin, stearic acids or salts thereof, magnesium or calcium sterate, talc, vegetable fats or oils, gums, glycols, or other known excipients. Such carriers may also include flavor and color additives or other ingredients. Compositions comprising such carriers are formulated by well known conventional methods. Depending on the intended mode of administration and the intended use, the compositions may be in the form of solid, semi-solid, or liquid dosage forms, such, for example, as powders, granules, crystals, liquids, suspensions, liposomes, pastes, cremes, salves, etc., and may be in unit-dosage forms suitable for administration of relatively precise dosages. Such compositions may contain about 0.005-100% active ingredient, more preferably about 0.5-25%. The concentration of active ingredients in these formulations can vary widely, and will be selected primarily by intended use, viscosities, etc., in accordance with the particular mode of administration selected. The composition or formulation to be administered will, in any event, contain a quantity of the vitamin-D analogue sufficient to achieve the desired therapeutic or prophylactic effect in the subject being treated. Typical compositions include delayed, or controlled release formulations, which may be delayed or controlled by pharmaceutical formulation techniques or by various salt forms known in the art.

The pharmaceutical compositions will be administered by parenteral or oral administration for prophylactic and/or therapeutic treatment. The pharmaceutical compositions can be administered in a variety of unit dosage forms depending upon the method of administration. For example, unit dosage forms suitable for oral administration include powder, tablets, pills, capsules, trochees, and dragees.

The pharmaceutical compositions will often be administered intravenously. Thus, this invention provides compositions for intravenous administration which comprise a solution of the compound dissolved or suspended in an acceptable carrier, preferably an aqueous carrier. A variety of aqueous carriers can be used, e.g., water, buffered water, 0.4% saline, and the like. In some instances vitamin-D analogues are dissolved in an organic solvent (e.g., dimethylsulfoxide) and either applied directly or diluted into an aqueous solvent. Typically, vitamin-D analogues that are relatively lipophilic are dissolved in an organic solvent such as DMSO and, if desired, subsequently diluted into a more polar solvent, such as water. These compositions will sometimes be sterilized by conventional, well known sterilization techniques, or can preferably be sterile filtered. The resulting aqueous solutions can be packaged for use as is, or lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally about 0.001-95% of active ingredient, preferably about 20%.

The compositions containing the compounds can be administered for prophylactic and/or therapeutic treatments. In therapeutic applications, compositions are administered to a patient already suffering from a disease, as described above, in an effective therapeutic amount sufficient to cure or at least partially arrest the symptoms of the disease and its complications. An amount adequate to accomplish this is defined as "therapeutically effective amount or dose." Amounts effective for this use will depend on the severity of the disease and the weight and general physiological state of the patient.

In prophylactic applications, compositions containing the compounds of the invention are administered to a patient susceptible to or otherwise at risk of a particular disease. Such an amount is defined to be a "prophylactically effective amount or dose." In this use, the precise amounts again depend on the patient's state of health and weight.

For solid compositions, conventional non-toxic solid excipients include, for example, pharmaceutical grades of mannitol, lactose, starch, magnesium stearate, talcum, celluloses, glucose, sucrose, magnesium carbonate, and the like may be used. The active compound as defined above may be formulated as suppositories using, for example, triglycerides, for example, any pharmaceutically acceptable Hard Fat NF bases (e.g., WITEPSOL™, Condea Vista Company, Cranford, N.J.), as the carrier. Liquid pharmaceutically administrable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington: The Science and Practice of Pharmacy*, Ed. Randy Hendrickson, Lippincott, Williams & Wilkins, 21$^{st}$ Edition (2005). The composition or formulation to be administered will, in any event, contain an effective amount of the active compound(s).

For oral administration, a pharmaceutically acceptable non-toxic composition is formed by the incorporation of any of the normally employed excipients, such as, for example pharmaceutical grades of mannitol, lactose, starch, magnesium stearate, talcum, celluloses, glucose, sucrose, magnesium, carbonate, and the like. Such compositions take the form of solutions, suspensions, tablets, capsules, powders, sustained release formulations and the like. Such compositions may contain about 0.01-95% active ingredient, preferably about 1-70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. Nos. 5,629,008, 5,851,547, 6,183,461, and 3,710,795, which are incorporated herein by reference.

Once detectable improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms or as a prophylactic measure to prevent disease symptom recurrence. In particular embodiments extended release formulations are contemplated.

The invention further includes therapeutic compositions comprising delayed or sustained release monolayered or bilayered formulations of a heterocyclic vitamin D analog of the invention. In this embodiment, the oral medicament includes a heterocyclic vitamin D analog of the invention in a sustained release matrix. Such matrices are known to those skilled in the art.

In another aspect, the heterocyclic vitamin D analogs may be prepared in liposomal/nanoparticle formulations for therapeutic administration in order to lower toxicity and maintain efficacy. The analogs can be complexed with liposomes in general, which can be, for example, made from hydrogenated soy phosphatidylcholine, distearoylphosphatidyglycerol and cholesterol. Liposomes and liposomal formulations and the methods and manner of making them are well known in the art. See for example Fahr and Seelig, Liposomal Formulations of Cyclosporin A: A Biophysical Approach to Pharmacokinetics and Pharmacodynamics, in *Critical Reviews in Therapeutic Drug Carrier Systems* 2 (2001), the teachings of which are incorporated by reference.

In yet another aspect, we contemplate that other chemotherapeutic, anti-inflammatory, anti-angiogenic, anti-fungal, amoebecidal, or anti-bacterial agents antiviral, may be co-administered with the heterocyclic vitamin D analogs of the invention to treat the above mentioned diseases or conditions or in a situation where multiple complications threaten the well being of a human. Exemplary agents include platinum drugs (cisplatin, carboplatin, oxaloplatin), doxorubicin, camptothecin analogs, Doxil, taxane derivatives, angiostatins, combretostatins, DBP-maf and peptides thereof, anti-VEGFR antibodies, ketoconazole, tinidazole, aspirin, naproxen, celecoxib amongst others.

In yet another aspect, we contemplate that heterocyclic vitamin D analogs of the invention could be used as sensitizers to radiation therapy to treat the above mentioned diseases or conditions.

Example 1

Synthesis of 6(S),19-(4-phenyl-3,5-dioxo-1,2,4-traizolidine-1,2-diyl)-3β-hydroxy-9,10-secoergosta-5 (10),7(E),22(E) triene (1)

To ergocalciferol (0.50 g) in EtOAc (15 mL at 0° C. under an argon atmosphere was added 4-phenyl-1,2,4-traizoline-3, 5-dione (0.24 g, 1.1 eq) in ethyl acetate (15 mL) over a period a 10 min. The mixture was stirred at 0° C. for three hours. Next the solvent was evaporated under reduced pressure. The residue obtained was purified by liquid column chromatography over neutral alumina and eluted with 1-4% MeOH in DCM. Homogeneous fractions were collected and concentrated under reduced pressure to afford title compound (1). Yield: 0.60 gm; MS m/e: 571.

Example 2

Synthesis of 6(S),19-(4-phenyl-3,5-dioxo-1,2,4-traizolidine-1,2-diyl)-3-β(bromoacetoxy)-9,10-seco-ergosta-5(10),7(E),22(E)triene (2)

DCC (12.8 mg, 0.000062 M) was added to a solution of bromoacetic acid (8.7 mg, 0.000062 M) in DCM (10 mL) at 0° C. under an argon atmosphere. The mixture was stirred for 30 min. To this solution the 3β-hydroxyl-adduct (1) (18 mg, 0.0000315 M) formed in previous step (see above), DMAP (10 mg, catalytic) and the pyridine (1.0 mg) was added. The reaction mixture was stirred for two hours at 0° C. under an argon atmosphere. Thereafter the reaction mixture was allowed to be warmed up to 22° C. (room temperature) and stirred for another 1-2 hours. The reaction mixture was then diluted with DCM (10 mL) and extracted with water. The organic layer was collected, dried over anhydrous sodium sulphate and concentrated under reduced pressure to afford a residue which was purified by preparative TLC using 3% MeOH in DCM as the eluent. The relevant bands were scratched and the compound was collected as a solution after separation of the compounds from silica gel with 5% MeOH in DCM. Upon concentration under reduced pressure the process yielded the title compound (2) as a white solid. Yield: 20 mg, MS m/e: 692.

Example 3

Biologic: Activity of HEVD Analogs

HEVD analogs were synthesized and screened for their biological activities. Screening identified several biological activities including anti-proliferative, cytotoxic, apoptosis inducing and anti-angiogenic activities against various human malignant cells and endothelial cells. These compounds are potent anti-proliferative agents against various human carcinomas as demonstrated by the results of a standard viability assay. Graphs illustrate these results (FIGS. 1-2).

Example 4

Evaluation of the Cytotoxicity of HEVD Analogs on Cancer Cells 5000 cancer cells ovarian cell (SKOV-3), or prostate cancer cells (PC3) maintained in DMEM media (InVitrogen, Carlsbad, Calif.), were plated in a 96 well plate. The cells were allowed to attach and proliferate for 24 hrs before treating them with HEVD analogs dissolved in ethanol and serially diluted to obtain the desired concentrations (0, 0.625, 1, 25, 2.5, 5, 10, 20 μM). At the end of 48 hrs of incubation, cell viability was estimated using the MTS Cell Titer 96 Aqueous One Kit (Promega Corp., Madison, Wis.) as recommended by the manufacturer.

Any references cited in this application are hereby incorporated by reference in their entirety for the substance of their disclosure. Those skilled in the art will recognize or be able to ascertain using no more than routine experimentation many equivalents of the specific embodiments of the invention described above. Such equivalents are intended to be encompassed herein.

What is claimed is:

1. A compound of formula 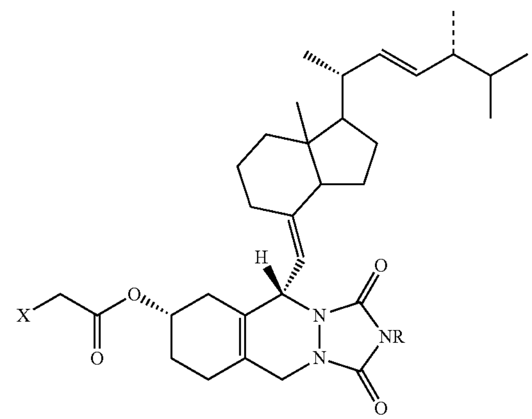 wherein X is Br, R is methyl or phenyl.

2. The compound of claim 1 where R is methyl.

3. The compound or claim 1 where R is phenyl.

* * * * *